United States Patent
Park

(10) Patent No.: US 12,203,863 B2
(45) Date of Patent: Jan. 21, 2025

(54) CARBOXYLIC ACID FUNCTIONALIZED 3-DIMENSIONAL SERS SUBSTRATE

(71) Applicant: PICO FOUNDRY INC., Daejeon (KR)

(72) Inventor: Hyung Joon Park, Seoul (KR)

(73) Assignee: PICO FOUNDRY INC., Daejeon (KR)

( * ) Notice: Subject to any disclaimer, the term of this patent is extended or adjusted under 35 U.S.C. 154(b) by 503 days.

(21) Appl. No.: 17/595,623

(22) PCT Filed: May 20, 2019

(86) PCT No.: PCT/KR2019/006023
§ 371 (c)(1),
(2) Date: May 5, 2022

(87) PCT Pub. No.: WO2020/235702
PCT Pub. Date: Nov. 26, 2020

(65) Prior Publication Data
US 2023/0288341 A1    Sep. 14, 2023

(51) Int. Cl.
*G01N 33/553* (2006.01)
*G01N 21/65* (2006.01)
*G01N 33/543* (2006.01)

(52) U.S. Cl.
CPC ..... *G01N 21/658* (2013.01); *G01N 33/54366* (2013.01); *G01N 33/553* (2013.01)

(58) Field of Classification Search
CPC .................................................. G01N 21/658
See application file for complete search history.

(56) References Cited

U.S. PATENT DOCUMENTS

| 2006/0038990 A1* | 2/2006 | Habib | G01N 21/658 |
| | | | 356/301 |
| 2011/0063610 A1 | 3/2011 | Ivanov et al. | |
| 2013/0196449 A1 | 8/2013 | Kim et al. | |

FOREIGN PATENT DOCUMENTS

| KR | 10-2014-0140179 A | 12/2014 |
| KR | 10-2017-0032093 A | 3/2017 |
| KR | 10-2018-0069980 A | 6/2018 |

OTHER PUBLICATIONS

Kari Thorkelsson, "Self-assembly and applications of anisotropic nanomaterials: A review", Jan. 23, 2015, (Year: 2015).*
International Search Report for PCT/KR2019/006023, dated Feb. 19, 2020.

* cited by examiner

*Primary Examiner* — Maurice C Smith
(74) *Attorney, Agent, or Firm* — Sughrue Mion, PLLC

(57) ABSTRACT

Disclosed is a carboxylic acid-functionalized 3-dimensional SERS substrate. A carboxylic acid-functionalized 3-dimensional SERS substrate according to an embodiment of the present invention includes a substrate; a 3-dimensional nanostructure including a multistacked metal nanowire array formed by alternately and repeatedly transfer printing a single-layer metal nanowire array, laminated on a polymer mold on which a pattern of a master mold is duplicated, onto the substrate 110 to be perpendicular to each other; and a functionalized carboxylic acid into which a residue of the polymer mold present on the 3-dimensional nanostructure is functionalized and which enables a target analyte to immobilize.

25 Claims, 18 Drawing Sheets

[FIG. 1]
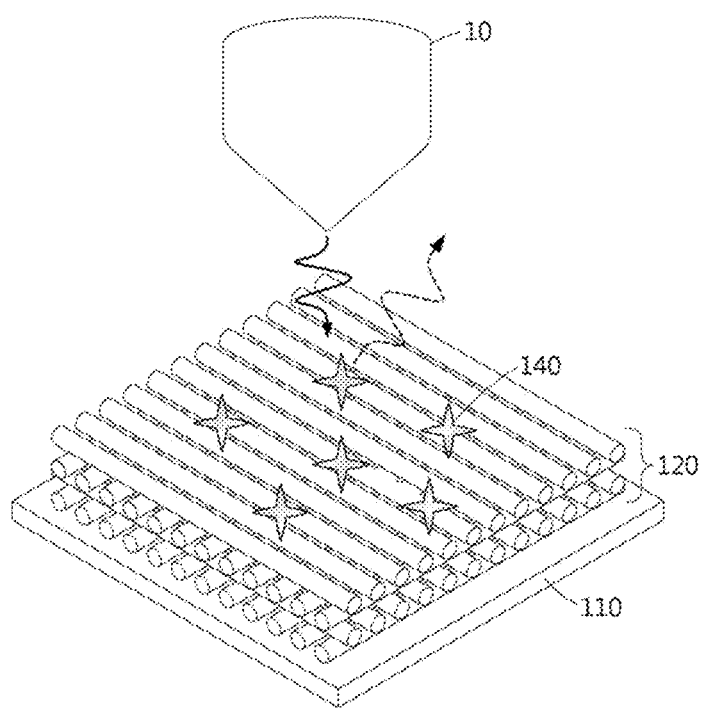

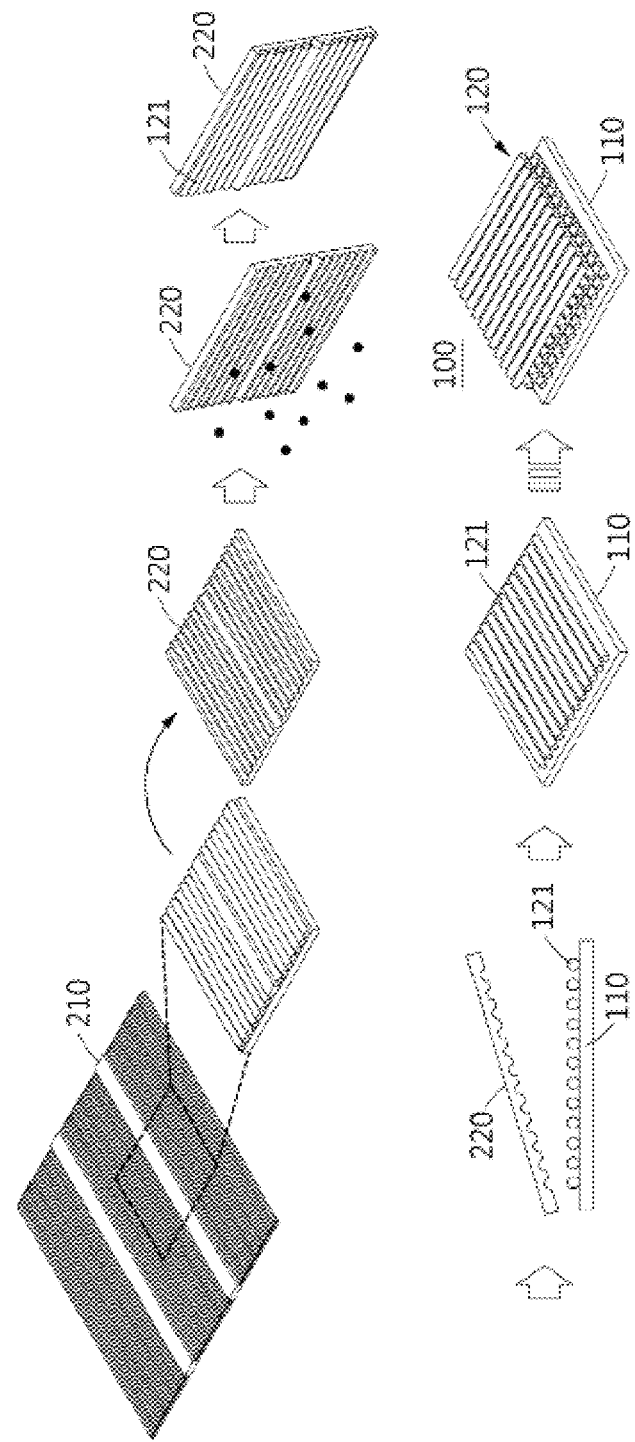
[FIG. 2]

[FIG. 3]
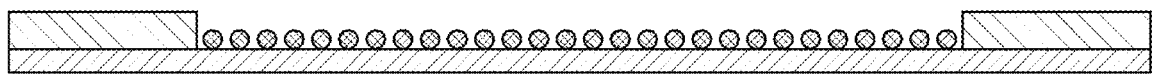
210
[FIG. 4a]
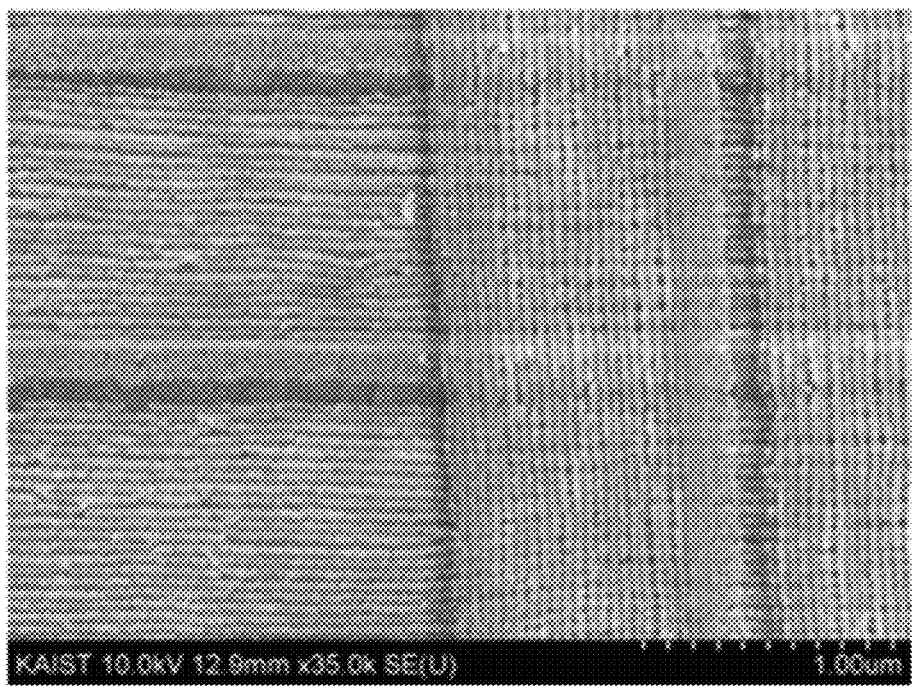

[FIG. 4b]
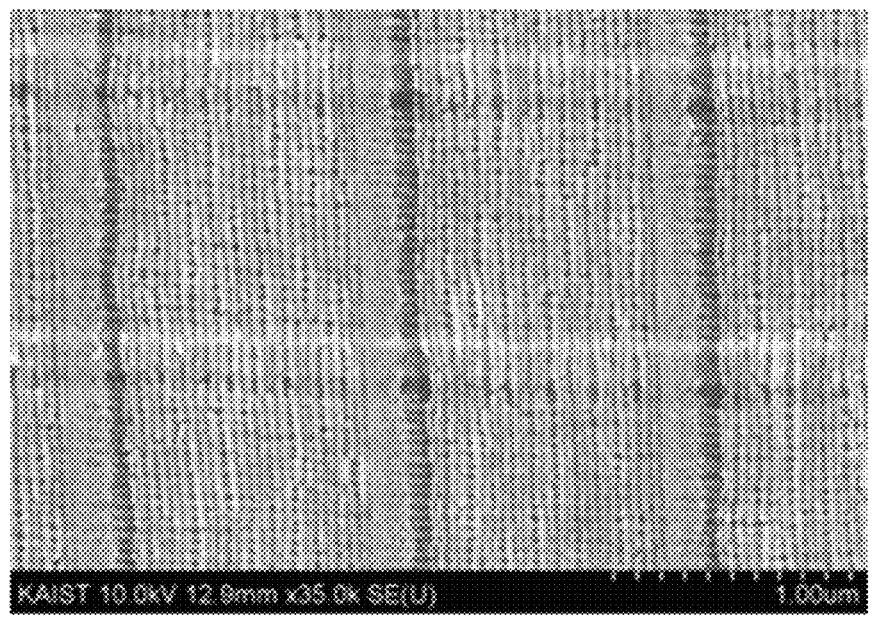
[FIG. 4c]
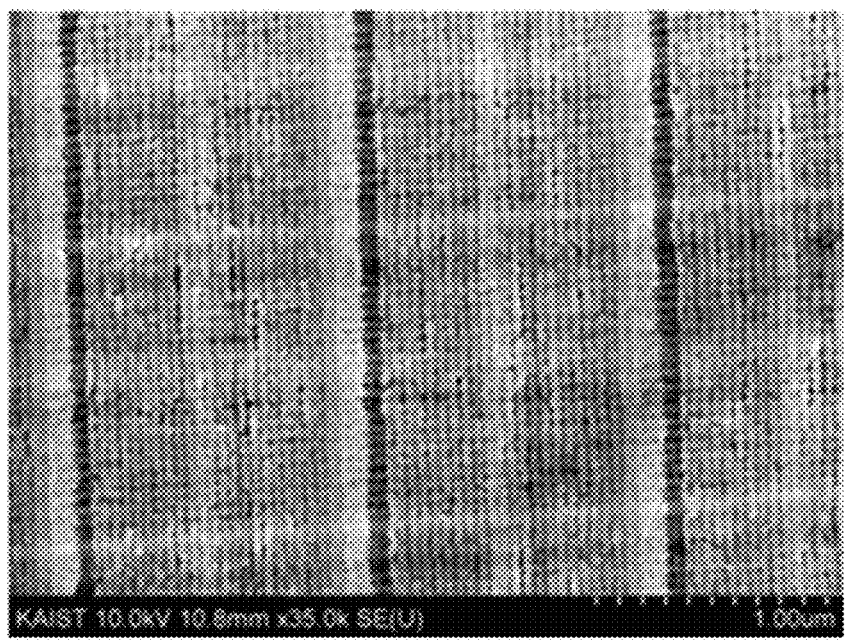

[FIG. 5]
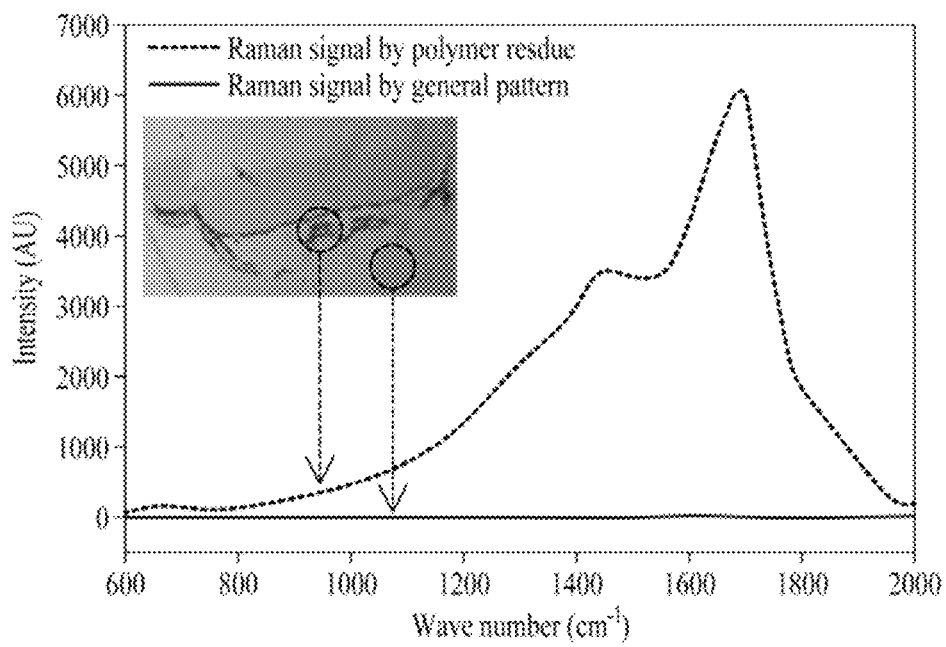
[FIG. 6]
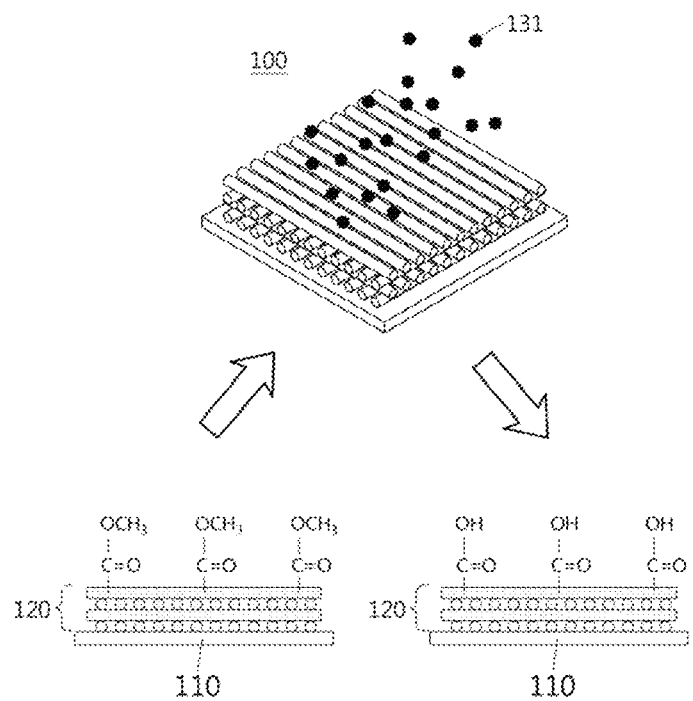

[FIG. 7]
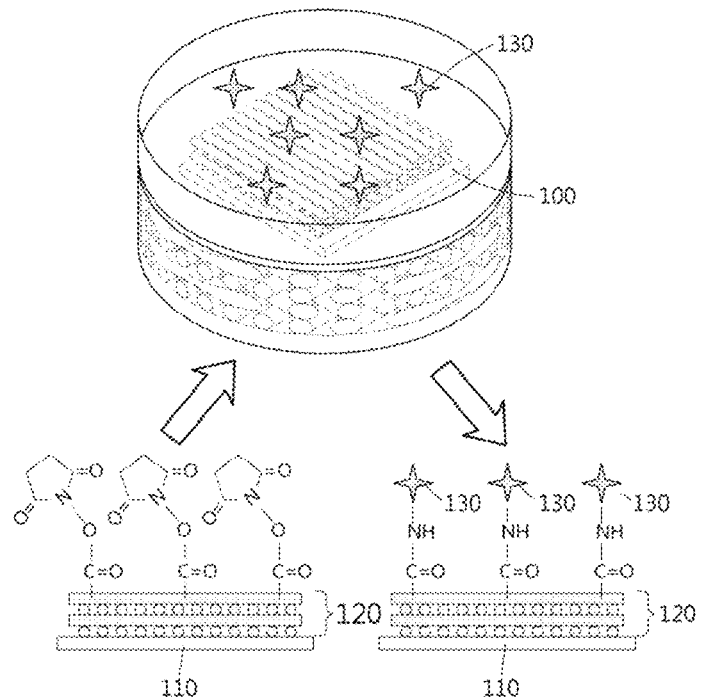
[FIG. 8a]
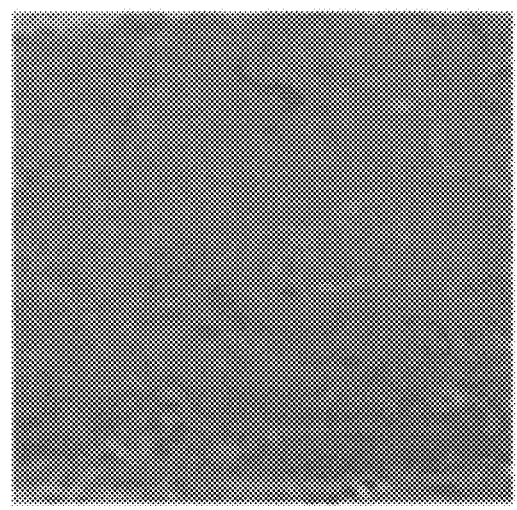

[FIG. 8b]
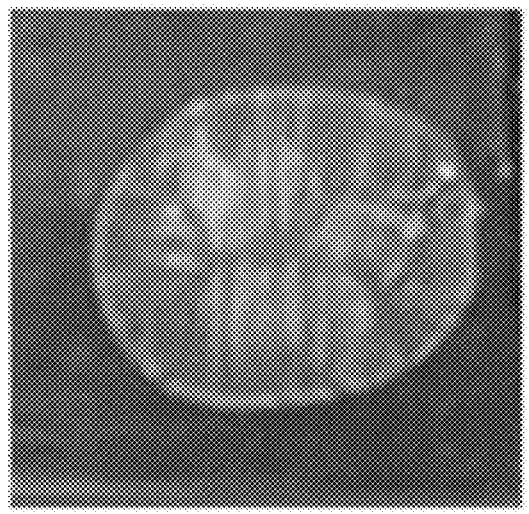
[FIG. 9a]
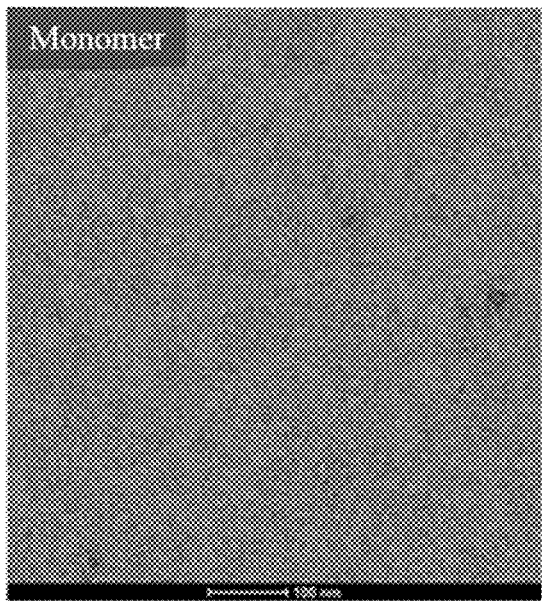

【FIG. 9b】
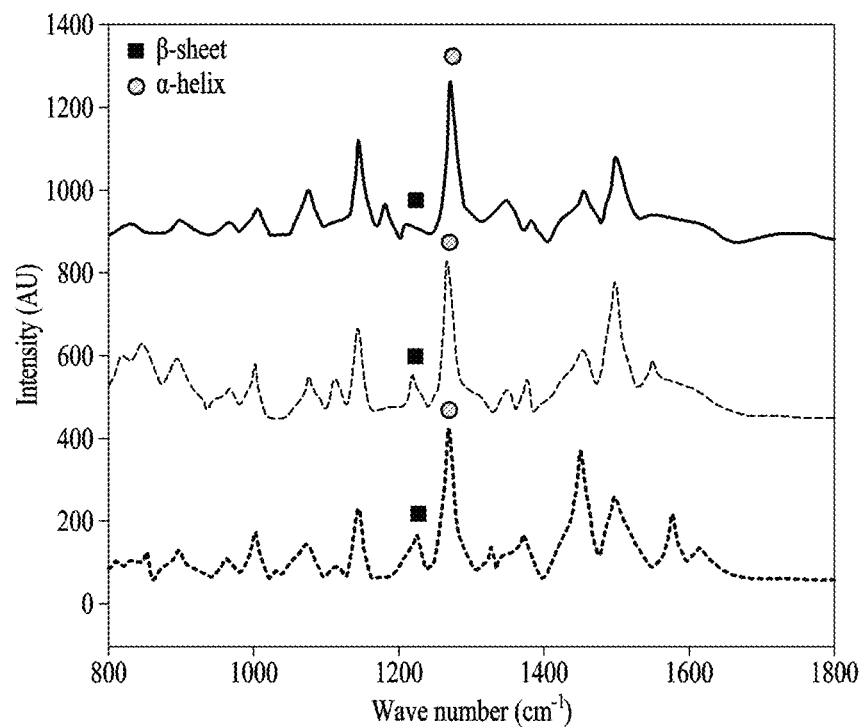
【FIG. 10a】
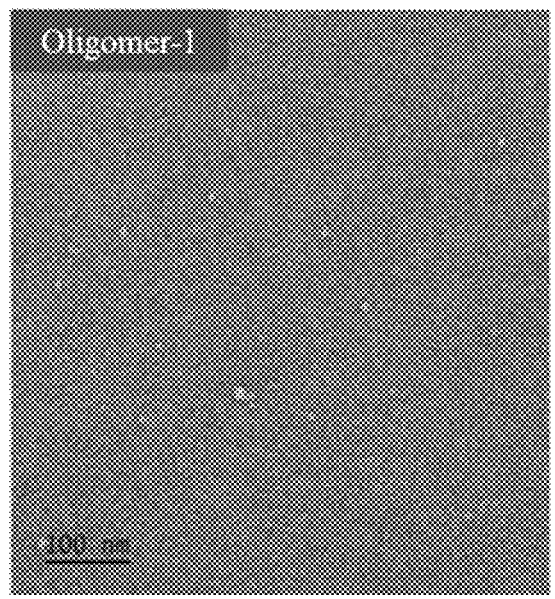

[FIG. 10b]
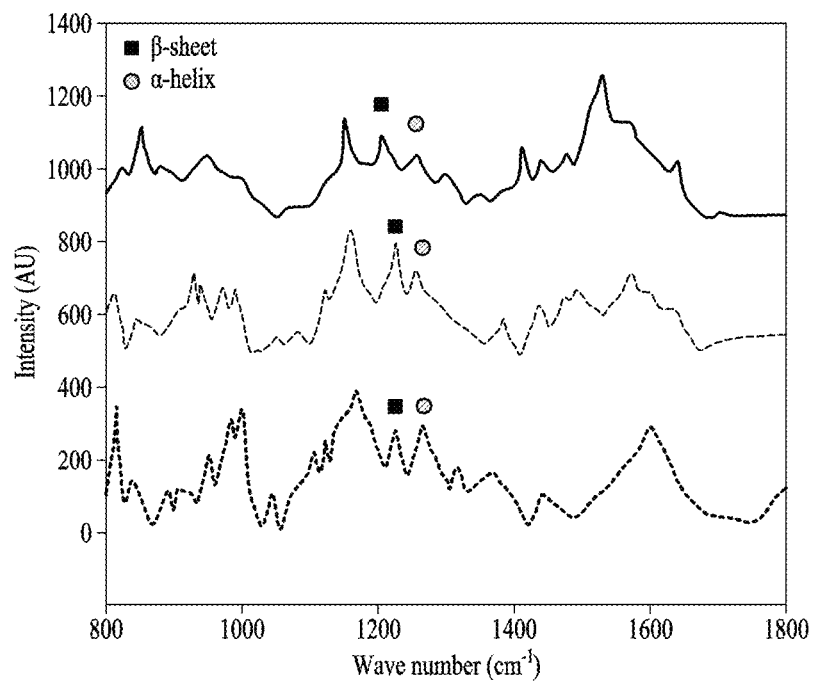
[FIG. 11a]
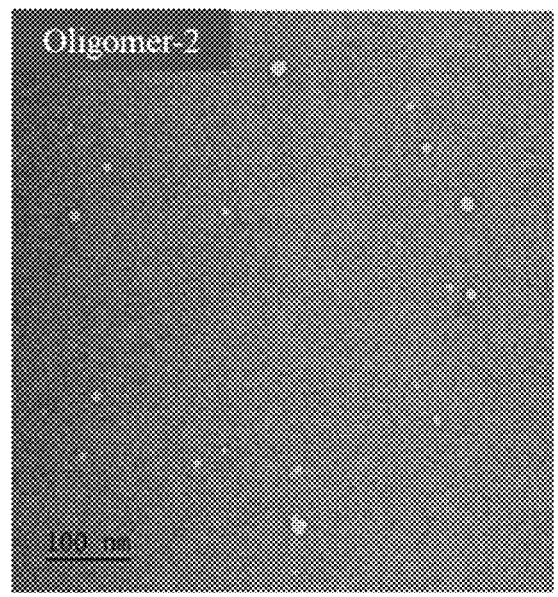

[FIG. 11b]
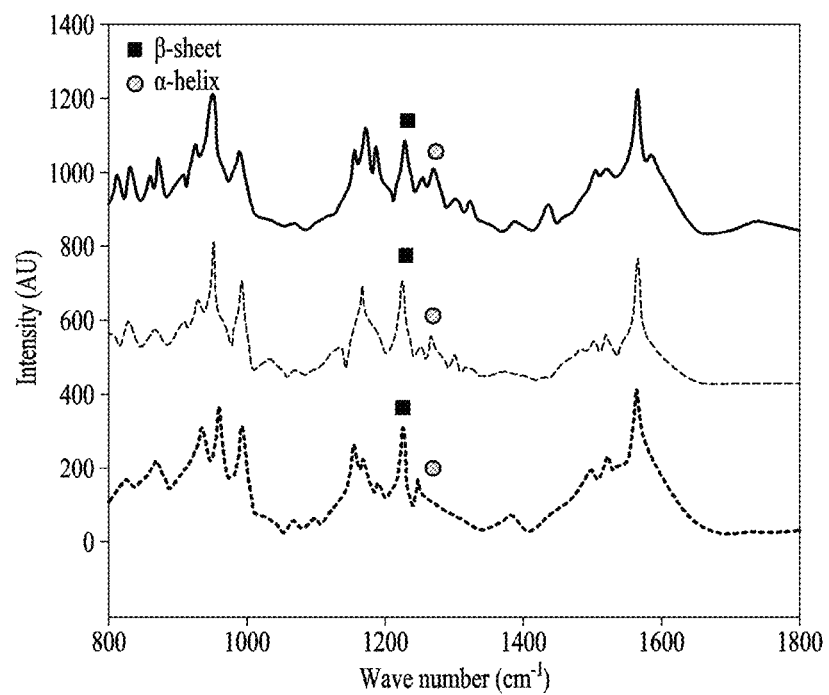
[FIG. 12]
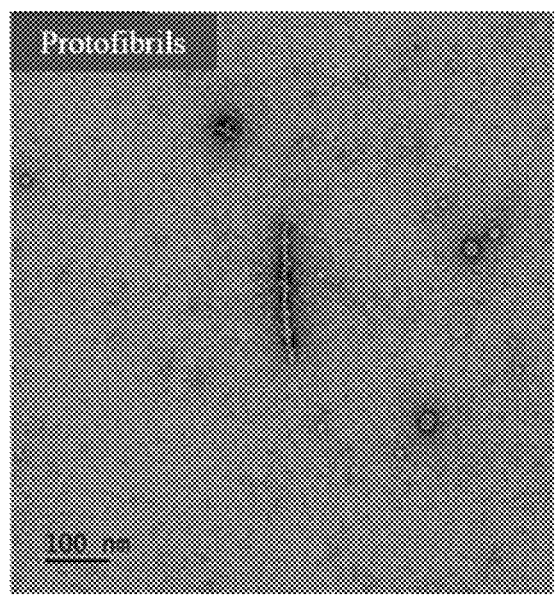

[FIG. 13]
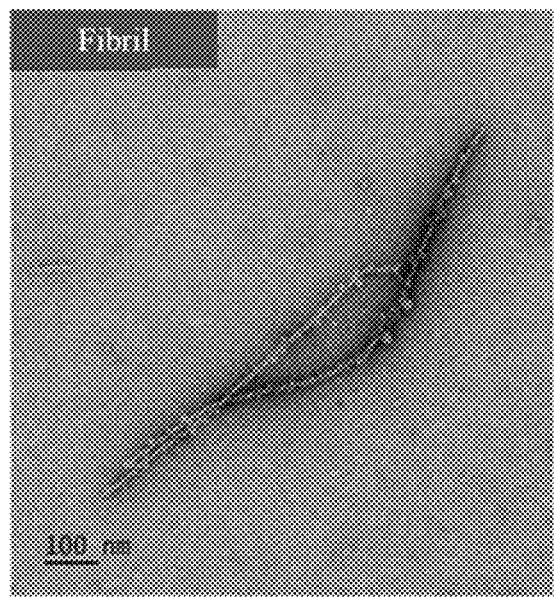
[FIG. 14]
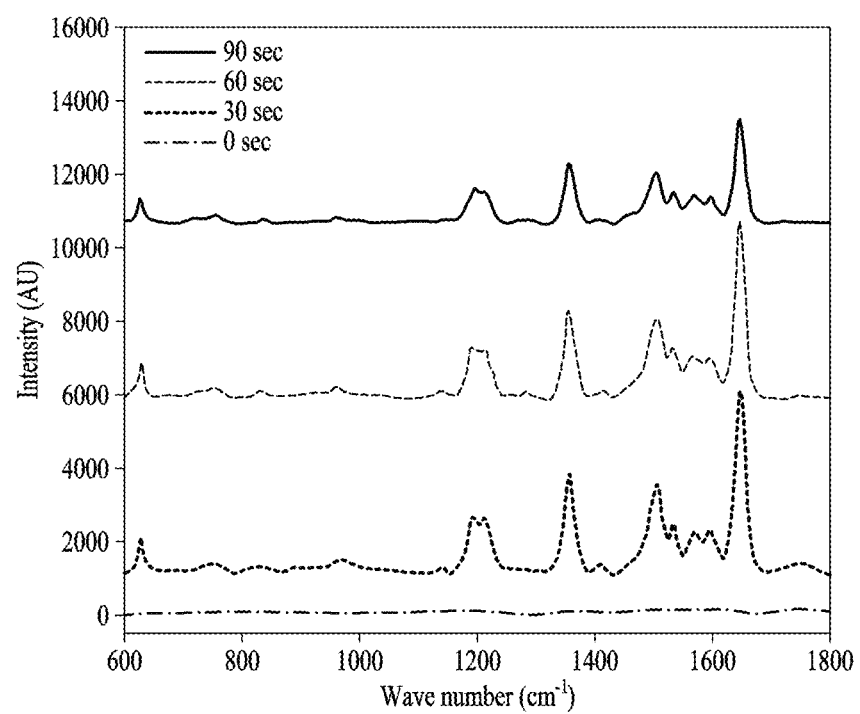

[FIG. 15]
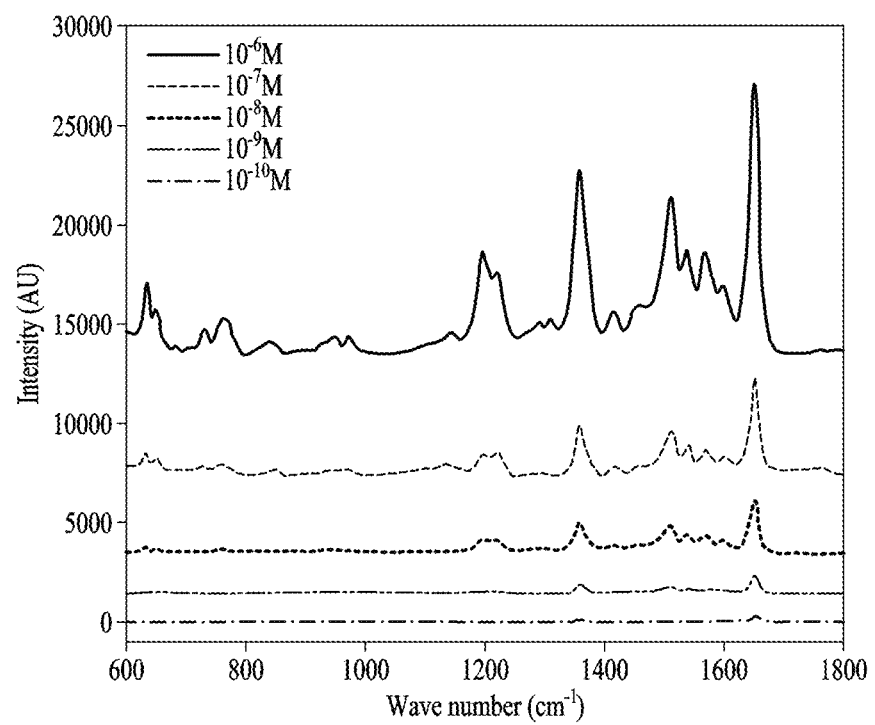

[FIG. 16]
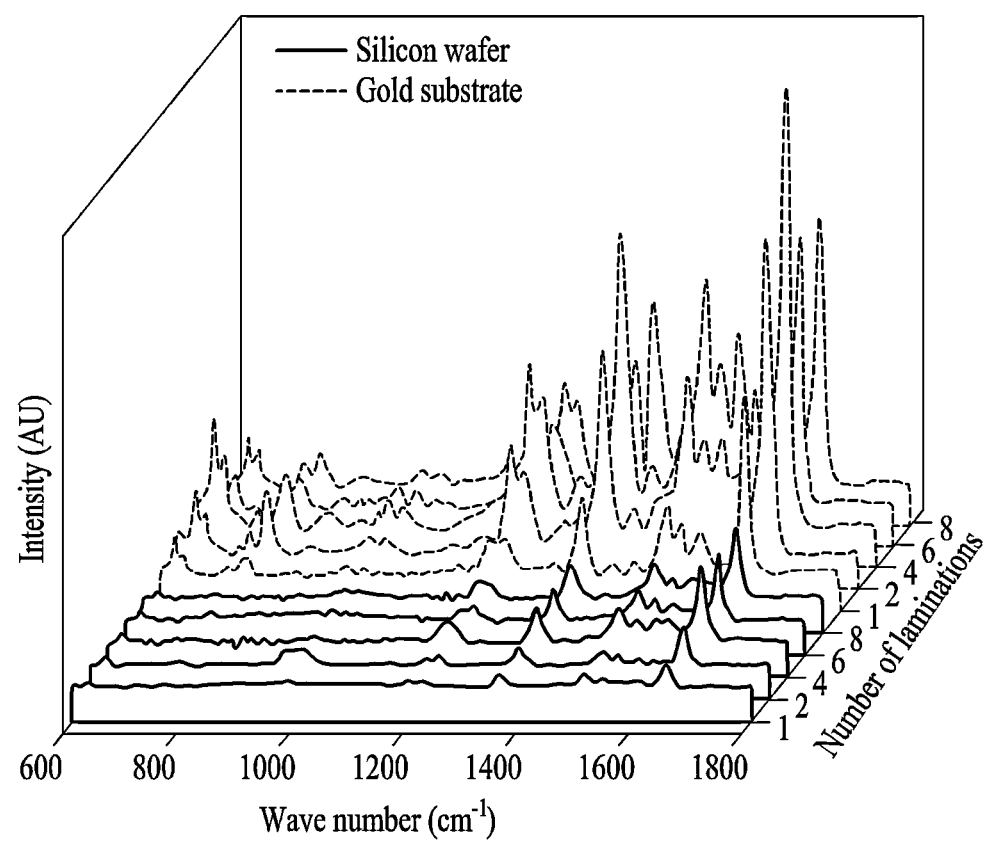

【FIG. 17】
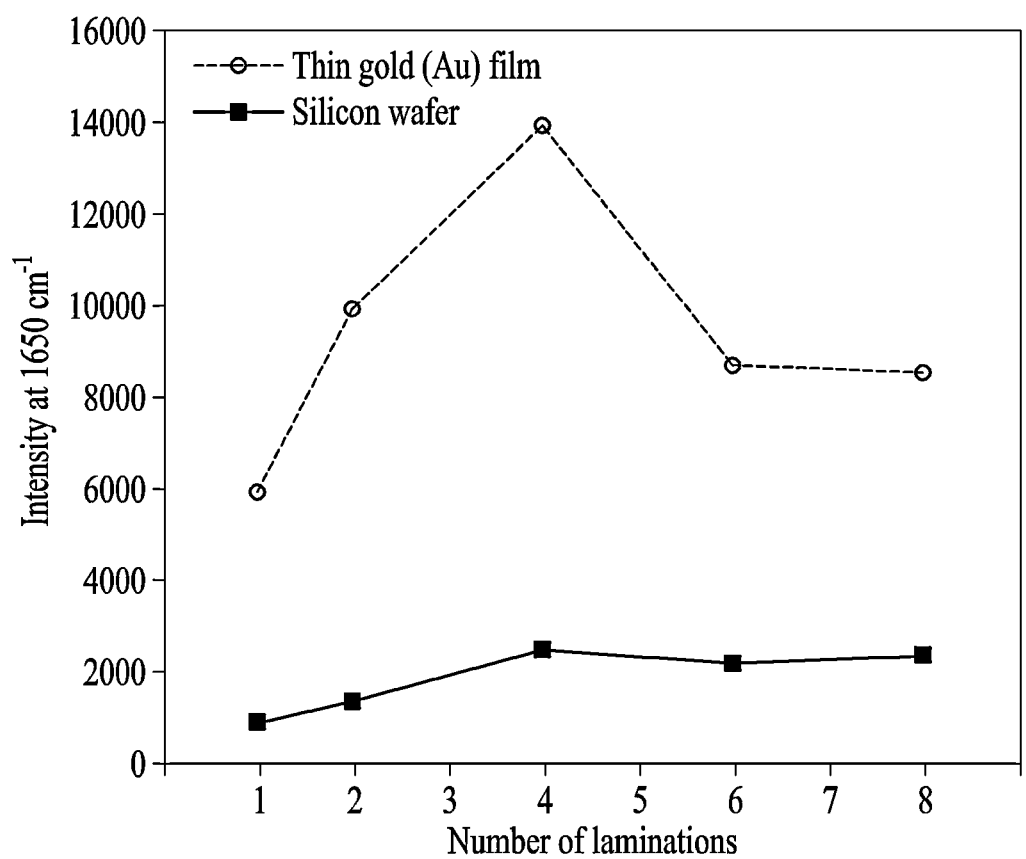

[FIG. 18]
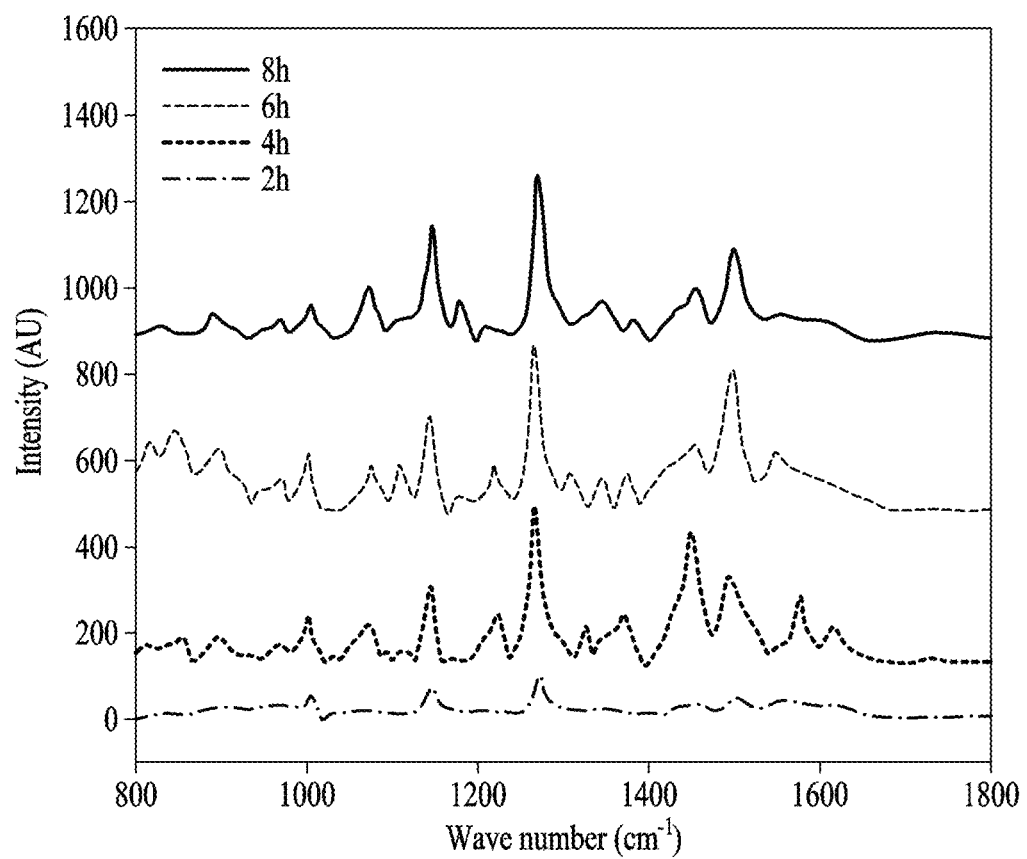

[FIG. 19]
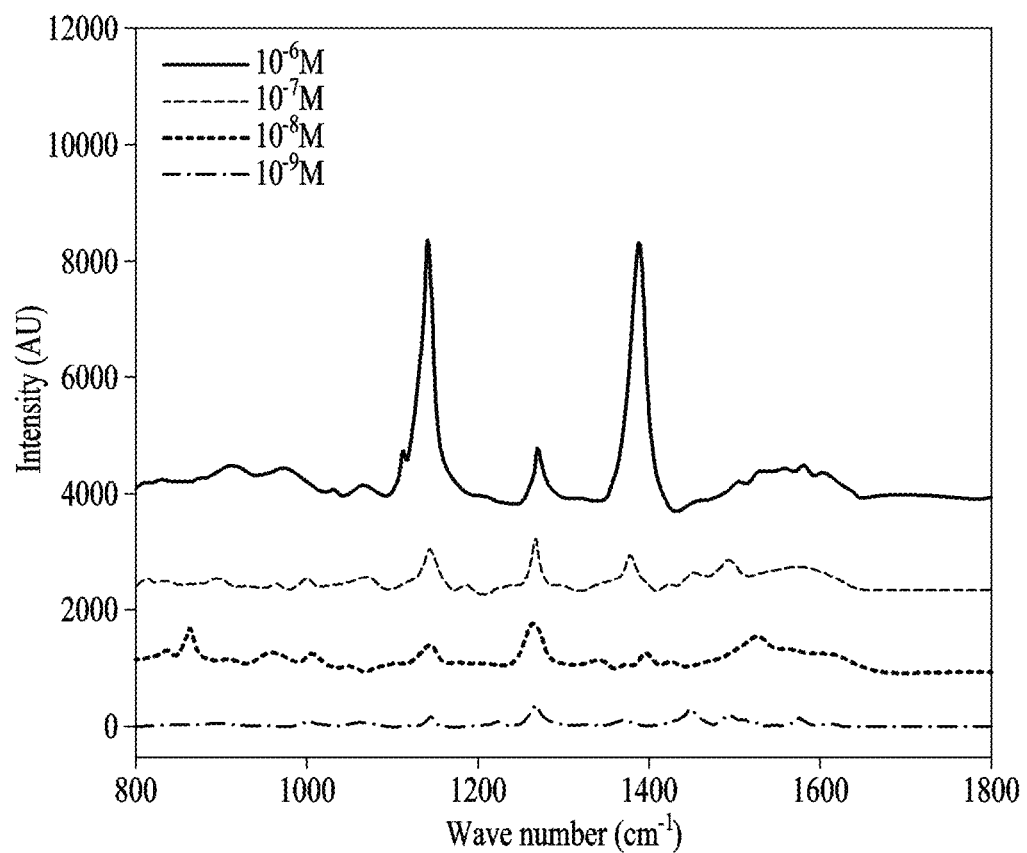

[FIG. 20]
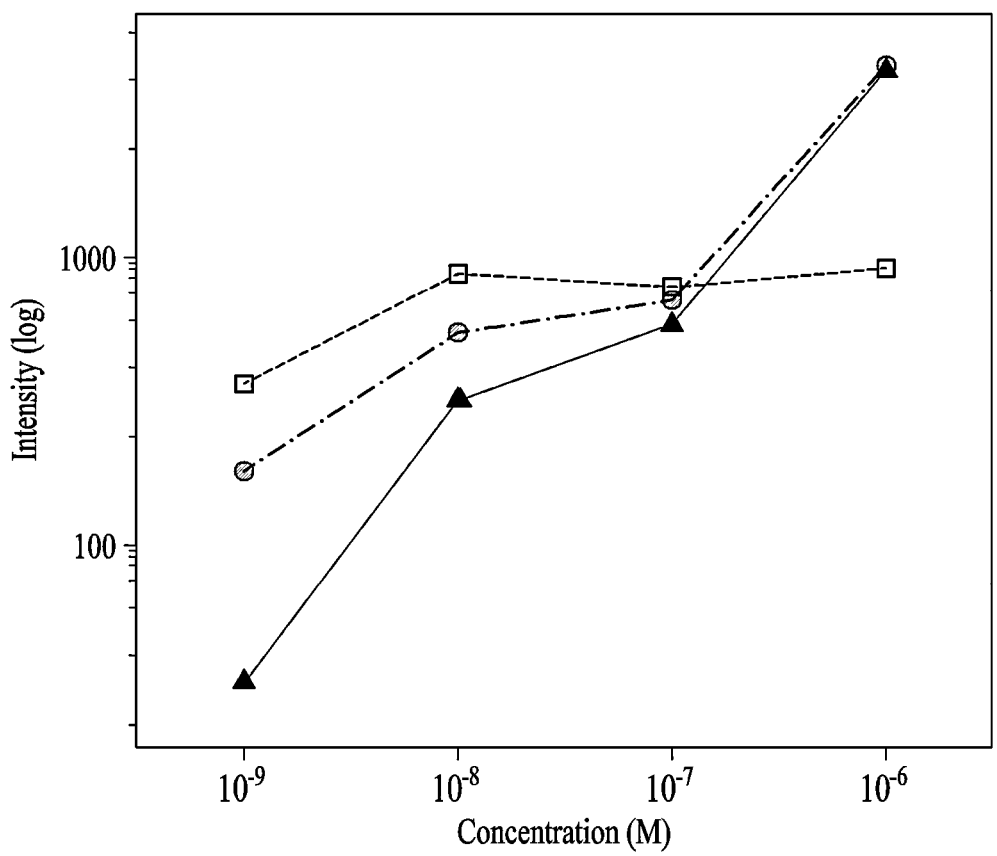

[FIG. 21]
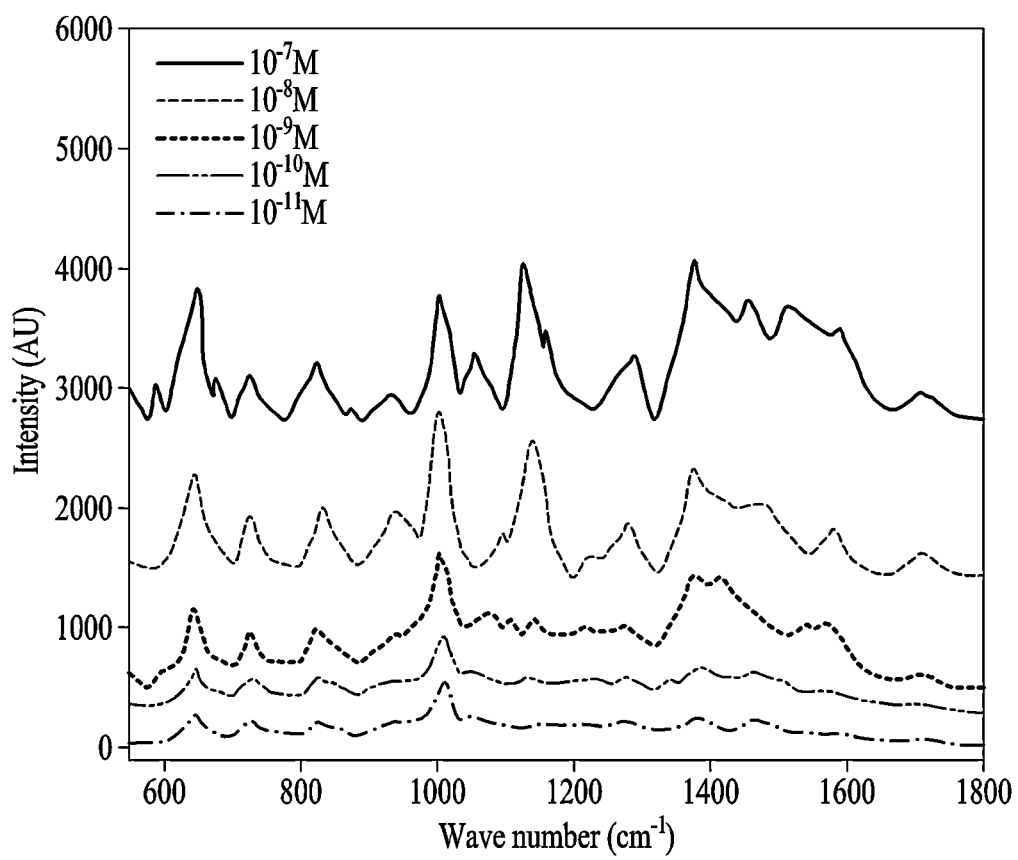

CARBOXYLIC ACID FUNCTIONALIZED 3-DIMENSIONAL SERS SUBSTRATE

CROSS-REFERENCE TO RELATED APPLICATION

This application is a National Stage Entry of PCT International Application No. PCT/KR2019/006023, which was filed on May 20, 2019, and the disclosure of which is incorporated herein by reference.

TECHNICAL FIELD

The present invention relates to a carboxylic acid-functionalized 3-dimensional SERS substrate.

BACKGROUND ART

Alzheimer's disease (AD) is a representative disease that causes dementia in humans.

According to previous studies, bacterial and β-amyloid accumulation between nerve cells (neurons) in the brain is known to cause Alzheimer's.

The protein β-amyloid is a peptide composed of 36 to 42 amino acids that is formed when amyloid precursor protein (APP) is degraded by β and γ secretases.

Misfolded β-amyloid monomers are prone to self-aggregation to form oligomers and protofibrils.

In addition, the tau protein is suspected to cause Alzheimer's by being phosphorylated and aggregated to form neurofibrillary tangles in neurons.

Among various studies on β-amyloid and tau proteins, there is great interest in the precise structure determination of β-amyloid and tau proteins.

Since the interactions between polypeptide chains are governed by the structural features of proteins, elucidating protein structure is a key step in elucidating how proteins aggregate.

Studies to elucidate these protein structures are mainly carried out by X-ray, NMR and Cryo-EM.

In recent years, direct acquisition of Raman spectra from proteins has been extensively studied, but small Raman cross sections and denaturation of proteins make it difficult to obtain Raman spectra directly.

By using the Raman spectrum measured directly from a protein, it is possible to obtain important information about the structural change in a protein more conveniently than conventional analysis methods.

With the recent advent of SERS with the aid of nanotechnology, active research has been conducted on obtaining surface enhancement Raman spectroscopy (SERS) spectrum directly from a protein without labeling.

SERS is considered as a promising alternative for protein structure studies.

Such a research field is generally referred to as label-free SERS. The SERS phenomenon is generated by plasmonic nanostructures that enhance the local electric field (E-field) at the interface between a metal and a dielectric, and can amplify the Raman signal several times.

One of representative platforms for label-free SERS is a solution-phase SERS that generates strong local electric fields by nanoparticle aggregation in a solution state.

A target analyte and nanoparticles dispersed in a liquid are surrounded by nanoparticles that generate a strong electromagnetic field on the surface of an aggregated target analyte by an external force.

Large molecules such as proteins are suitable as a subject of SERS generated in a solution state.

However, poor protein reproducibility, structural change, and denaturation are considered as problems of solution-phase SERS.

Another important factor in protein structure analysis is a SERS substrate fabricated by the nanolithography process.

Enhanced local electric fields generated from nanowires, nanoparticles and 3D nanostructures amplify the Raman signal, but hinder the feasibility of protein analysis.

In addition, it is very difficult to place large molecules, such as proteins, in a locally enhanced E-field region, and the coffee-ring effect is one of factors hindering the drop coating of a target analyte on a SERS substrate.

RELATED ART DOCUMENTS

Patent Documents

Korean Patent No. 10-1930514, "METHOD OF MANUFACTURING SUBSTRATE FOR SERS USING ANODIC ALUMINUM OXIDATION AND SUBSTRATE FOR SERS MANUFACTURED THEREBY"

Korean Patent No. 10-1776103, "A SERS substrate using synthetic resin material and a method for manufacturing the same"

DISCLOSURE

Technical Problem

Therefore, the present invention has been made in view of the above problems, and it is one object of the present invention to provide a carboxylic acid-functionalized 3-dimensional SERS substrate configured to include a 3-dimensional nanostructure formed by alternately transfer printing and laminating a metal nanowire array on a substrate to be perpendicular to each other, thereby being capable of efficiently increasing a Raman analysis signal.

It is another object of the present invention to provide a carboxylic acid-functionalized 3-dimensional SERS substrate that is subjected to an amine coupling reaction after functionalizing a surface of the 3-dimensional nanostructure into carboxylic acid such that a target analyte satisfactorily binds to the surface of the 3-dimensional nanostructure.

It is another object of the present invention to provide a carboxylic acid-functionalized 3-dimensional SERS substrate whose carboxylic acid-functionalized 3-dimensional nanostructure effectively binds to a target analyte, thereby being capable of detecting a target analyte at low concentration.

It is another object of the present invention to provide a carboxylic acid-functionalized 3-dimensional SERS substrate capable of providing fibrillation information that represents an oligomerization state of β-amyloid and tau protein by SERS measurement using Alzheimer's biomarkers, β-amyloid and tau protein, as target analytes.

It is another object of the present invention to provide a carboxylic acid-functionalized 3-dimensional SERS substrate capable of informing the onset and progression of Alzheimer's based on fibrillation information on β-amyloid and tau protein, as target analytes, by SERS measurement.

It is another object of the present invention to provide a carboxylic acid-functionalized 3-dimensional SERS substrate capable of efficiently increasing a Raman analysis signal for a carboxylic acid-functionalized 3-dimensional SERS substrate by controlling a lamination number of a metal nanowire array.

It is yet another object of the present invention to provide a high-performance carboxylic acid-functionalized 3-dimensional SERS substrate having high signal enhancement effect at a low cost, excellent signal uniformity and reproducibility by forming a metal nanowire array, instead of performing a lithography process, and by performing nanotransfer printing on a substrate.

Technical Solution

In accordance with an aspect of the present invention, the above and other objects can be accomplished by the provision of a carboxylic acid-functionalized 3-dimensional SERS substrate, including: a substrate; a 3-dimensional nanostructure including a multistacked metal nanowire array formed by alternately and repeatedly transfer printing a single-layer metal nanowire array, laminated on a polymer mold on which a pattern of a master mold is duplicated, onto the substrate 110 to be perpendicular to each other; and a functionalized carboxylic acid into which a residue of the polymer mold present on the 3-dimensional nanostructure is functionalized and which enables a target analyte to immobilize.

According to the carboxylic acid-functionalized 3-dimensional SERS substrate according to an embodiment of the present invention, a residue of the thin polymer film present on the 3-dimensional nanostructure may be functionalized into carboxylic acid by a functionalization process.

According to the carboxylic acid-functionalized 3-dimensional SERS substrate according to an embodiment of the present invention, the functionalized carboxylic acid may be functionalized into carboxylic acid (—COOH) by performing a reaction ion etching (RIE) process for the thin polymer film present on the 3-dimensional nanostructure.

According to the carboxylic acid-functionalized 3-dimensional SERS substrate according to an embodiment of the present invention, the metal nanowire array of the 3-dimensional nanostructure may be laminated 4 to 10 times.

According to the carboxylic acid-functionalized 3-dimensional SERS substrate according to an embodiment of the present invention, metal nanowires in the metal nanowire array may have a diameter of 25 nm to 50 nm.

According to the carboxylic acid-functionalized 3-dimensional SERS substrate according to an embodiment of the present invention, the 3-dimensional nanostructure may be formed by, after manufacturing the polymer mold using a thin polymer film and adhesive film on coated on a master mold on which a pattern is formed, forming the metal nanowire array on the polymer mold, and then selectively weakening adhesive force between the adhesive film and the polymer mold so that the metal nanowire array on the polymer mold is transfer printed onto the substrate.

According to the carboxylic acid-functionalized 3-dimensional SERS substrate according to an embodiment of the present invention, the polymer mold may be prepared by, after uniformly attaching the adhesive film to one surface of the thin polymer film formed on the master mold, separating the adhesive film-attached thin polymer film from the master mold.

According to the carboxylic acid-functionalized 3-dimensional SERS substrate according to an embodiment of the present invention, the polymer mold and adhesive film on which the metal nanowire array is formed may be brought into contact with the polymer pad such that the metal nanowire array is in contact with a polymer pad, the polymer pad on which the metal nanowire array remains may be brought into contact with the substrate such that the metal nanowire array is in contact with the substrate after separating the polymer mold and the adhesive film from the polymer pad such that the metal nanowire array remains on the polymer pad, and the polymer pad may be separated from the substrate to be transfer printed.

In accordance with another aspect of the present invention, there is provided a carboxylic acid-functionalized 3-dimensional SERS substrate, including: a substrate; a 3-dimensional nanostructure including a multistacked metal nanowire array formed by alternately and repeatedly transfer printing a single-layer metal nanowire array, laminated on a polymer mold on which a pattern of a master mold is duplicated, onto the substrate 110 to be perpendicular to each other; and a functionalized carboxylic acid into which a residue of the polymer mold present on the 3-dimensional nanostructure is functionalized and which enables a target analyte to immobilize, wherein the functionalized carboxylic acid is modified into an amine group through amine coupling reaction to immobilize the target analyte.

According to the carboxylic acid-functionalized 3-dimensional SERS substrate according to an embodiment of the present invention, a residue of the thin polymer film present on the 3-dimensional nanostructure may be functionalized into carboxylic acid by a functionalization process, and the functionalized carboxylic acid may be functionalized into carboxylic acid (—COOH) by performing a reaction ion etching (RIE) process for the thin polymer film present on the 3-dimensional nanostructure.

According to the carboxylic acid-functionalized 3-dimensional SERS substrate according to an embodiment of the present invention, the amine coupling reaction may be performed by reacting a coupling agent including 1-ethyl-3-(3-dimethylaminopropyl)-carbodiimide (EDC) and N-hydroxysuccinimide (NHS) with the functionalized carboxylic acid.

According to the carboxylic acid-functionalized 3-dimensional SERS substrate according to an embodiment of the present invention, the amine coupling reaction may be performed at 4° C. to 10° C. for 4 hours to 8 hours.

According to the carboxylic acid-functionalized 3-dimensional SERS substrate according to an embodiment of the present invention, the target analyte may include β-amyloid or tau protein.

According to the carboxylic acid-functionalized 3-dimensional SERS substrate according to an embodiment of the present invention, a Raman analysis signal generated from the 3-dimensional nanostructure may include fibrillation information on the target analyte.

According to the carboxylic acid-functionalized 3-dimensional SERS substrate according to an embodiment of the present invention, the target analyte may have a concentration of $10^{-12}$M or more.

According to the carboxylic acid-functionalized 3-dimensional SERS substrate according to an embodiment of the present invention, the metal nanowire array of the 3-dimensional nanostructure may be laminated 4 to 10 times.

According to the carboxylic acid-functionalized 3-dimensional SERS substrate according to an embodiment of the present invention, metal nanowires in the metal nanowire array may have a diameter of 25 nm to 50 nm.

According to the carboxylic acid-functionalized 3-dimensional SERS substrate according to an embodiment of the present invention, the 3-dimensional nanostructure may be formed by, after manufacturing the polymer mold using a thin polymer film and adhesive film on coated on a master mold on which a pattern is formed, forming the metal nanowire array on the polymer mold, and then selectively weakening adhesive force between the adhesive film and the polymer mold so that the metal nanowire array on the polymer mold is transfer printed onto the substrate.

According to the carboxylic acid-functionalized 3-dimensional SERS substrate according to an embodiment of the present invention, the polymer mold may be prepared by, after uniformly attaching the adhesive film to one surface of the thin polymer film formed on the master mold, separating the adhesive film-attached thin polymer film from the master mold.

According to the carboxylic acid-functionalized 3-dimensional SERS substrate according to an embodiment of the present invention, the polymer mold and adhesive film on which the metal nanowire array is formed may be brought into contact with the polymer pad such that the metal nanowire array is in contact with a polymer pad, the polymer pad on which the metal nanowire array remains may be brought into contact with the substrate such that the metal nanowire array is in contact with the substrate after separating the polymer mold and the adhesive film from the polymer pad such that the metal nanowire array remains on the polymer pad, and the polymer pad may be separated from the substrate to be transfer printed.

Advantageous Effects

In accordance with an embodiment of the present invention, a Raman analysis signal can be efficiently increased by alternately transfer printing and laminating a metal nanowire array on a substrate to be perpendicular to each other so as to form a 3-dimensional nanostructure.

In accordance with an embodiment of the present invention, a target analyte can satisfactorily bind to a surface of the 3-dimensional nanostructure by performing an amine coupling reaction after functionalizing the surface of the 3-dimensional nanostructure into carboxylic acid.

In accordance with an embodiment of the present invention, the carboxylic acid-functionalized 3-dimensional nanostructure satisfactorily binds to a target analyte, so that a target analyte at low concentration can be detected.

In accordance with an embodiment of the present invention, fibrillation information representing an oligomerization state of β-amyloid and tau protein can be provided by SERS measurement using Alzheimer's biomarkers, β-amyloid and tau protein, as target analytes.

In accordance with an embodiment of the present invention, the onset and progression of Alzheimer's can be informed from fibrillation information on β-amyloid and tau protein, as target analytes, by SERS measurement.

In accordance with an embodiment of the present invention, a Raman analysis signal for the carboxylic acid-functionalized 3-dimensional SERS substrate can be efficiently increased by controlling a lamination number of a metal nanowire array.

In accordance with an embodiment of the present invention, a high-performance SERS substrate having high signal enhancement effect at a low cost, excellent signal uniformity and reproducibility can be provided by forming a metal nanowire array, instead of performing a lithography process, and by performing nanotransfer printing on a substrate.

DESCRIPTION OF DRAWINGS

FIG. 1 illustrates a perspective view of a carboxylic acid-functionalized 3-dimensional SERS substrate according to an embodiment of the present invention.

FIG. 2 is a schematic diagram illustrating a process of forming a 3-dimensional nanostructure on a substrate according to an embodiment of the present invention.

FIG. 3 illustrates a sectional view of a master mold according to an embodiment of the present invention.

FIG. 4a illustrates a scanning electron microscope (SEM) image of a single-layered 3-dimensional nanostructure according to an embodiment of the present invention taken from a plane.

FIG. 4b illustrates an SEM image, taken from a plane, of a 3-dimensional nanostructure formed by laminating a metal nanowire array according to an embodiment of the present invention twice.

FIG. 4c illustrates an SEM image, taken from a plane, of a 3-dimensional nanostructure formed by laminating a metal nanowire array according to an embodiment of the present invention four times.

FIG. 5 illustrates a Raman spectrum of a 3-dimensional nanostructure according to an embodiment of the present invention.

FIG. 6 is a schematic diagram illustrating a process of functionalizing a surface of a 3-dimensional nanostructure according to an embodiment of the present invention into carboxylic acid.

FIG. 7 is a schematic diagram illustrating an amine coupling process of a carboxylic acid-functionalized 3-dimensional nanostructure according to an embodiment of the present invention.

FIG. 8a is an optical microscope image illustrating a state in which an amine-coupled 3-dimensional nanostructure according to an embodiment of the present invention is dip-coated on a target analyte and combined with the target analyte.

FIG. 8b is an optical microscope image illustrating a state in which the amine-coupled 3-dimensional nanostructure according to an embodiment of the present invention is drop-coated on a target analyte and combined with the target analyte.

FIG. 9a is a TEM image illustrating monomers of a target analyte according to an embodiment of the present invention.

FIG. 9b illustrates a Raman spectrum of monomers of a target analyte according to an embodiment of the present invention.

FIG. 10a is a TEM image illustrating oligomer type 1 of a target analyte according to an embodiment of the present invention.

FIG. 10b illustrates a Raman spectrum of oligomer type 1 of the target analyte according to an embodiment of the present invention.

FIG. 11a is a TEM image illustrating oligomer type 2 of a target analyte according to an embodiment of the present invention.

FIG. 11b illustrates a Raman spectrum of oligomer type 2 of the target analyte according to an embodiment of the present invention.

FIG. 12 is a TEM image illustrating a protofibril shape of a target analyte according to an embodiment of the present invention.

FIG. 13 is a TEM image illustrating a fibril shape of a target analyte according to an embodiment of the present invention.

FIG. 14 illustrates RIE process time-dependent SERS spectra of a carboxylic acid-functionalized 3-dimensional SERS substrate according to an embodiment of the present invention.

FIG. 15 illustrates target analyte concentration-dependent SERS spectra of a carboxylic acid-functionalized 3-dimensional SERS substrate according to an embodiment of the present invention.

FIG. 16 illustrates metal nanowire array lamination number-dependent SERS spectra of a carboxylic acid-functionalized 3-dimensional SERS substrate according to an embodiment of the present invention.

FIG. 17 illustrates substrate type-dependent SERS intensity of a carboxylic acid-functionalized 3-dimensional SERS substrate according to an embodiment of the present invention.

FIG. 18 illustrates reaction time-dependent SERS spectra of a carboxylic acid-functionalized 3-dimensional SERS substrate according to an embodiment of the present invention.

FIG. 19 illustrates β-amyloid concentration-dependent SERS spectra of a carboxylic acid-functionalized 3-dimensional SERS substrate according to an embodiment of the present invention.

FIG. 20 illustrates β-amyloid concentration-dependent SERS intensity according to an embodiment of the present invention.

FIG. 21 illustrates tau protein concentration-dependent SERS spectra of a carboxylic acid-functionalized 3-dimensional SERS substrate according to an embodiment of the present invention.

BEST MODE

The present invention will now be described more fully with reference to the accompanying drawings and contents disclosed in the drawings. However, the present invention should not be construed as limited to the exemplary embodiments described herein.

The terms used in the present specification are used to explain a specific exemplary embodiment and not to limit the present inventive concept. Thus, the expression of singularity in the present specification includes the expression of plurality unless clearly specified otherwise in context. It will be further understood that the terms "comprise" and/or "comprising", when used in this specification, specify the presence of stated components and/or steps, but do not preclude the presence or addition of one or more other components and/or steps thereof.

It should not be understood that arbitrary aspects or designs disclosed in "embodiments", "examples", "aspects", etc. used in the specification are more satisfactory or advantageous than other aspects or designs.

In addition, the expression "or" means "inclusive or" rather than "exclusive or". That is, unless otherwise mentioned or clearly inferred from context, the expression "x uses a or b" means any one of natural inclusive permutations.

In addition, as used in the description of the disclosure and the appended claims, the singular form "a" or "an" is intended to include the plural forms as well, unless context clearly indicates otherwise.

Although terms used in the specification are selected from terms generally used in related technical fields, other terms may be used according to technical development and/or due to change, practices, priorities of technicians, etc. Therefore, it should not be understood that terms used below limit the technical spirit of the present invention, and it should be understood that the terms are exemplified to describe embodiments of the present invention.

Also, some of the terms used herein may be arbitrarily chosen by the present applicant. In this case, these terms are defined in detail below. Accordingly, the specific terms used herein should be understood based on the unique meanings thereof and the whole context of the present invention.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

In addition, in the following description of the present invention, a detailed description of known functions and configurations incorporated herein will be omitted when it may make the subject matter of the present invention unclear. The terms used in the specification are defined in consideration of functions used in the present invention, and can be changed according to the intent or conventionally used methods of clients, operators, and users. Accordingly, definitions of the terms should be understood on the basis of the entire description of the present specification.

A carboxylic acid-functionalized 3-dimensional SERS substrate according to the present invention is fabricated by functionalizing a 3-dimensional nanostructure, formed by laminating a metal nanowire array on a substrate several times, into the form of carboxylic acid. As the functionalized carboxylic acid binds to a target analyte, the presence or absence of the target analyte may be determined by checking a peak corresponding to the target analyte during SERS analysis.

FIG. 1 illustrates a perspective view of a carboxylic acid-functionalized 3-dimensional SERS substrate according to an embodiment of the present invention.

Referring to FIG. 1, a carboxylic acid-functionalized 3-dimensional SERS substrate 100 according to an embodiment of the present invention includes a substrate 110, a 3-dimensional nanostructure 120 and a functionalized carboxylic acid derived from the 3-dimensional nanostructure 120.

The substrate 110 is a working surface on which the 3-dimensional nanostructure 120 according to an embodiment of the present invention is to be formed.

The substrate 110 may be formed of, without being limited to, any of a polymer film, glass and a ceramic material.

In accordance with an embodiment, the substrate 110 may be coated with any one of gold (Au), silver (Ag), copper (Cu), nickel (Ni), platinum (Pt), chromium (Cr), cobalt (Co), and palladium (Pd).

The 3-dimensional nanostructure 120 according to an embodiment of the present invention may be formed on the substrate 110.

The 3-dimensional nanostructure 120 includes a multistacked metal nanowire array 121 formed by alternately and repeatedly transfer printing a single-layer metal nanowire array 121, laminated on the polymer mold 220 on which a pattern of a master mold 210 is duplicated, onto the substrate 110 to be perpendicular to each other.

In accordance with an embodiment, the polymer mold 220 may be formed of PMMA.

In accordance with an embodiment, metal (221) nanowires of the metal nanowire array 121 may have a diameter of 25 nm to 50 nm.

In accordance with an embodiment, the metal nanowire array 121 may be formed of the metal (221) nanowires having the same or different diameters.

In accordance with an embodiment, the 3-dimensional nanostructure 120 may be formed by laminating the metal nanowire array 121 4 to 10 times.

In accordance with an embodiment, the 3-dimensional nanostructure 120 may be formed of, without being limited to, any one of gold (Au), silver (Ag), copper (Cu), nickel (Ni), platinum (Pt), chromium (Cr), cobalt (Co), palladium (Pd) and an alloy of gold and silver.

The target analyte 130 is immobilized on the carboxylic acid-functionalized 3-dimensional SERS substrate 100 according to an embodiment of the present invention, and a laser irradiated from an objective lens 10 may detect a target analyte 130 using light scattered by the target analyte 130, i.e., a Raman analysis signal through SERS measurement.

Hereinafter, a process of forming the 3-dimensional nanostructure 120 according to an embodiment of the present invention is described with reference to FIG. 2.

FIG. 2 is a schematic diagram illustrating a process of forming a 3-dimensional nanostructure on a substrate according to an embodiment of the present invention.

Referring to FIG. 2, a polymer material is deposited on the master mold 210 to form the polymer mold 220 on which an engraved concave and convex pattern is formed.

In accordance with an embodiment, a thin polymer film is coated on the master mold 210 on which the pattern has been formed, and then the thin polymer film may be manufactured in the form of an adhesive film-attached thin polymer film using an adhesive film by the polymer mold 220.

Specifically, an adhesive film may be uniformly attached to one surface of the thin polymer film formed on the master mold 210, and then the adhesive film-attached thin polymer film may be separated from the master mold 210 to manufacture the polymer mold 220.

The thin polymer film is applied to the master mold 210 using at least one process of at least one process of spin coating, deep coating and spray coating, thereby having a concave and convex pattern.

In accordance with an embodiment, a polymer applied to the thin polymer film may have a solubility parameter of 20 MPa$^{1/2}$ to 40 MPa$^{1/2}$ and a glass transition temperature higher than room temperature.

Accordingly, the polymer may stably maintain a solid state at room temperature.

Next, a metal (221) material is selectively deposited on the engraved pattern of the polymer mold 220 to form the single-layer metal nanowire array 121.

The polymer mold 220 on which the single-layer metal nanowire array 121 has been formed is transfer printed onto the substrate 110.

Specifically, after positioning the polymer mold 220 such that the single-layer metal nanowire array 121 is in contact with the substrate 110, the polymer mold 220 is only removed so that the single-layer metal nanowire array 121 is formed on the substrate 110.

Specifically, an organic solvent vapor may be injected between an adhesive film and the polymer mold 220 to weaken adhesive force between the adhesive film and the polymer mold 220.

Accordingly, the polymer mold 220 may be separated so that the metal nanowire array 121 remains on the substrate 110.

In accordance with an embodiment, the polymer mold 220 and adhesive film on which the metal nanowire array 121 has been formed may be brought in contact with the polymer pad such that the metal nanowire array 121 is in contact with the polymer pad (not shown).

Next, the polymer mold 220 and the adhesive film may be separated from the polymer pad so that the metal nanowire array 121 remains on the polymer pad.

Next, the polymer pad on which the metal nanowire array 121 remains is brought in contact with the substrate 110 such that the metal nanowire array 121 is in contact with the substrate 110, and then the polymer pad is separated from the substrate 110 to transfer print the metal nanowire array 121.

The 3-dimensional nanostructure 120 may be formed to include the multistacked metal nanowire arrays 121 by repeating the aforementioned process such that the metal nanowire arrays 121 are to be perpendicular to each other.

FIG. 3 illustrates a sectional view of a master mold according to an embodiment of the present invention.

Referring to FIG. 3, the master mold 210 may have concave and convex patterns having different heights.

The pattern of the master mold 210 may be formed using a patterning process including at least one of photolithography, block co-polymer self-assembly-based lithography and E-beam lithography, and a reactive ion etching (RIE) process.

The master mold 210 may be manufactured by directed self-assembly (DSA) of a block co-polymer (BCP).

In accordance with an embodiment, the master mold 210 may be coated with a PDMS brush polymer with low surface energy or a hydrophobic self-assembled monolayer (SAM) such as hexa methylene di silazane (HMDS) so that a surface of the master mold 210 has a low surface energy of 30 mJ/m$^2$ or less.

In accordance with an embodiment, the master mold 210 may be manufacture to have a concave and convex pattern with a line width of 15 nm and a line width of 8 nm by self-assembling a PS-PDMS block co-polymer on a silicon trench substrate 110 with a width of 1 um to 1 cm and a depth of 1 nm to 1 cm to form a linear surface pattern, and then by performing RIE process in an oxygen environment.

In accordance with an embodiment, the master mold 210 may be, without being limited to, a silicon wafer.

A specific fabrication method of the master mold 210 is described below with reference to the following examples.

FIG. 4*a* illustrates a scanning electron microscope (SEM) image of a single-layered 3-dimensional nanostructure according to an embodiment of the present invention taken from a plane, FIG. 4*b* illustrates an SEM image, taken from a plane, of a 3-dimensional nanostructure formed by laminating a metal nanowire array according to an embodiment of the present invention twice, and FIG. 4*c* illustrates an SEM image, taken from a plane, of a 3-dimensional nanostructure formed by laminating a metal nanowire array according to an embodiment of the present invention four times.

Referring to FIGS. 4*a* to 4*c*, the 3-dimensional nanostructure 120 according to an embodiment of the present invention is formed by alternately and repeatedly laminating the metal nanowire array 121 to be perpendicular to each other, thereby having a fabric-like shape when viewed from a plane.

Here, the metal (221) nanowires shown as relatively dark shades are metal (221) nanowires having a relatively large diameter.

A wave vector of a laser irradiated from the objective lens 10 is perpendicular to a surface of the carboxylic acid-functionalized 3-dimensional SERS substrate 100 according to an embodiment of the present invention.

By the laser, the free electron cloud of the metal (221) nanowires of the 3-dimensional nanostructure 120 horizontally vibrates.

In addition, a strong localized electromagnetic field is generated on a side of the metal (221) nanowires by the laser.

Since the metal nanowire arrays 121 of the 3-dimensional nanostructure 120 are respectively laminated at an angle of 90 degrees, the polarization dependence of excitation laser is negligible.

When a surface of the carboxylic acid-functionalized 3-dimensional SERS substrate 100 according to an embodiment of the present invention is observed by a scattering-type near-field optical microscope (s-NSOM), the carboxylic acid-functionalized 3-dimensional SERS substrate 100 shows surface plasmon polariton (SPP).

The scattering-type near-field optical microscope (s-NSOM), surface plasmon polariton visualizes how SPP behaves depending on important parameters.

Here, the surface plasmon polariton increases as the period of the metal (221) nanowires decreases and the number of laminations of the metal nanowire array 121 increases.

Accordingly, the 3-dimensional nanostructure 120 formed by cross-laminating the metal nanowire array 121 to be perpendicular to each other may variously polarize light to produce the maximum plasmon effect and may increase a Raman analysis signal generated from the 3-dimensional nanostructure 120.

In general, it is preferable to remove a residue of the polymer mold 220 existing on the surface by washing with acetone after transfer printing. However, it is almost impossible to completely remove the residue of the polymer mold 220.

As the single-layer metal nanowire array 121 laminated on the polymer mold 220 is transfer printed onto the substrate 110, a portion of the polymer mold 220 may remain on the surface of the metal nanowire array 121.

Specifically, after the single-layer metal nanowire array 121 laminated on the polymer mold 220 is brought in contact with the substrate 110, a residue of the polymer mold 220 may remain on the surface of the metal nanowire array 121 when the polymer mold 220 is separated from the metal nanowire array 121 in contact with the substrate 110.

Accordingly, a residue of the polymer mold 220 may remain on the surface of the 3-dimensional nanostructure 120 formed by alternately and repeatedly laminating the metal nanowire array 121, on which a residue of the polymer mold 220 remains, on the substrate 110 to be perpendicular to each other.

In accordance with an embodiment, a PMMA thin film, as the polymer mold 220, absorbs energy from light and is easily cured by cross-linking or graphitization.

Accordingly, once the PMMA thin film is cured, it is easy to peel the PMMA thin film from the substrate 110.

The metal nanowire array 121 formed on the polymer mold 220 may transfer thermal energy to the polymer mold 220 and may be cross-linked and graphitized.

FIG. 5 illustrates a Raman spectrum of a 3-dimensional nanostructure according to an embodiment of the present invention.

Here, the Raman spectrum of the 3-dimensional nanostructure 120 according to an embodiment of the present invention of FIG. 5 illustrates D and G bands of graphite.

In the image inserted in FIG. 5, a left circle denotes a location at which a Raman signal is measured.

Referring to FIG. 5, Raman analysis signals (Raman signal in normal pattern) of general surfaces of the 3-dimensional nanostructure 120 have a constant intensity.

However, in can be confirmed that, when a residue of the PMMA thin film as the polymer mold 220 remains on the surface of the 3-dimensional nanostructure 120, the Raman analysis signal (Raman signal in crumpled pattern) intensity is very large compared to those of general surfaces of the 3-dimensional nanostructure 120.

Specifically, a strong peak is observed between about 1400 $cm^{-1}$ and about 1700 $cm^{-1}$, which is due to the PMMA thin film residue present on the surface of the 3-dimensional nanostructure 120.

The residue of the polymer mold 220 present on the 3-dimensional nanostructure 120 may be functionalized into a carboxylic acid through a functionalization process, thereby immobilizing the target analyte 130.

Specifically, the residue of the thin polymer film present on the 3-dimensional nanostructure 120 may be functionalized into carboxylic acid by a process of reaction ion etching (RIE) the thin polymer film.

Hereinafter, functionalization of the 3-dimensional nanostructure 120 is described in detail with reference to FIG. 6.

FIG. 6 is a schematic diagram illustrating a process of functionalizing a surface of a 3-dimensional nanostructure according to an embodiment of the present invention into carboxylic acid.

Referring to FIG. 6, a residue of the polymer mold 220 present on the 3-dimensional nanostructure 120 has a —$COOCH_3$ functional group.

The redox reaction of the residue of the polymer mold 220 cured on the surface of the 3-dimensional nanostructure 120 occurs by an RIE process using an oxygen gas 131 so that $CH_3$ in —$COOCH_3$ of the residue of the polymer mold 220 is substituted with H and thus functionalized into carboxylic acid (—COOH).

The carboxylic acid-functionalized 3-dimensional nanostructure 120 according to an embodiment of the present invention may be coupled with an amine to immobilize the target analyte 130.

FIG. 7 is a schematic diagram illustrating an amine coupling process of a carboxylic acid-functionalized 3-dimensional nanostructure according to an embodiment of the present invention.

Referring to FIG. 7, a carboxylic acid-functionalized the 3-dimensional nanostructure 120 is modified to have an amine group through an amine coupling reaction according to an example, thereby immobilizing the target analyte 130.

The amine coupling reaction may be performed by reacting a coupling agent including 1-ethyl-3-(3-dimethylamino-propyl)-carbodiimide (EDC) and N-hydroxysuccinimide (NHS) with the functionalized carboxylic acid.

In accordance with an embodiment, the carboxylic acid-functionalized 3-dimensional SERS substrate 100 according to an embodiment of the present invention may be supported in the coupling agent solution so that an amine coupling reaction occurs and modification into an amine group occurs.

An amine-coupled 3-dimensional SERS substrate 110 binds the target analyte 130 to immobilize the target analyte 130.

FIG. 8a is an optical microscope image illustrating a state in which an amine-coupled 3-dimensional nanostructure according to an embodiment of the present invention is dip-coated on a target analyte and combined with the target analyte, and FIG. 8b is an optical microscope image illustrating a state in which the amine-coupled 3-dimensional nanostructure according to an embodiment of the present invention is drop-coated on a target analyte and combined with the target analyte.

Referring to FIGS. 8a and 8b, in the case of dip coating, a target analyte is immobilized by an amine coupling reaction in a petri dish. In this case, it can be confirmed that the amine-coupled 3-dimensional nanostructure is cleanly coated without a white precipitate on a surface thereof.

However, in the case of drop-coated, a target analyte is dropped using a pipette without an amine coupling reaction. In this case, it can be confirmed that the target analyte is thickly aggregated on the carboxylic acid-functionalized 3-dimensional SERS substrate according to an embodiment of the present invention.

In accordance with an embodiment, the target analyte 130 may refer to a biological protein.

Specifically, the target analyte 130 may include, without being limited to, β-amyloid or tau protein used to diagnose Alzheimer's disease.

According to an embodiment, when the target analyte 130 is β-amyloid or tau protein, the presence or absence of β-amyloid or tau protein may be determined through binding of the carboxylic acid-functionalized 3-dimensional SERS substrate 100 according to an embodiment of the present invention to the target analyte 130.

Accordingly, the presence or absence of β-amyloid or tau protein can be confirmed according to a Raman analysis signal generated through SERS using the carboxylic acid-functionalized 3-dimensional SERS substrate 100 according to an embodiment of the present invention, thereby being capable of diagnosing Alzheimer's.

Specifically, a Raman analysis signal generated from the 3-dimensional nanostructure 120 may include fibrillation information on the target analyte 130.

In accordance with an embodiment, the amine coupling reaction may be performed at 4° C. to 10° C. for 4 hours to 8 hours.

When a target analyte according to an embodiment of the present invention is β-amyloid, the target analyte may become easily fibrous. To prevent fibrosis, it is preferred to perform an amine coupling reaction at a low temperature such as 4° C. to 10° C.

When the target analyte 130 is subjected to SERS measurement using the carboxylic acid-functionalized 3-dimensional SERS substrate 100 according to an embodiment of the present invention, the concentration of the target analyte 130 may be $10^{-12}$M or more.

In other words, when the target analyte 130 is subjected to SERS measurement using the carboxylic acid-functionalized 3-dimensional SERS substrate 100 according to an embodiment of the present invention, a detection limit concentration of the target analyte 130 may be $10^{-12}$M.

The β-amyloid protein known as the cause of Alzheimer's disease has an α-helix structure when it is normal.

However, due to some cause, the α-helix structure of the β-amyloid protein is denatured into a β-sheet form.

As the β-amyloid of the α-helix structure and β-amyloid of the β-sheet structure are agglomerated with each other, β-amyloid monomers are aggregated into oligomers, protofibrils or fibrils to cause dementia symptoms.

Accordingly, a process that monomers of β-amyloid or tau protein change into oligomers may be traced according to a Raman analysis signal generated through SERS using the carboxylic acid-functionalized 3-dimensional SERS substrate 100 according to an embodiment of the present invention.

FIG. 9a is a TEM image illustrating monomers of a target analyte according to an embodiment of the present invention, and FIG. 9b illustrates a Raman spectrum of monomers of a target analyte according to an embodiment of the present invention.

Referring to FIGS. 9a and 9b, it can be confirmed that when the target analyte 130 bonded to the carboxylic acid-functionalized 3-dimensional SERS substrate 100 is a monomer, a Raman analysis signal peak in the α-helix structure is higher than that in the β-sheet.

FIG. 10a is a TEM image illustrating oligomer type 1 of a target analyte according to an embodiment of the present invention, and FIG. 10b illustrates a Raman spectrum of oligomer type 1 of the target analyte according to an embodiment of the present invention.

Referring to FIGS. 10a and 10b, it can be confirmed that when a target analyte 130 bonded to a carboxylic acid-functionalized 3-dimensional SERS substrate 100 is partially agglomerated and is oligomer type 1, a Raman analysis signal peak in the β-sheet structure is slightly higher than a Raman analysis signal peak in the α-helix structure.

In addition, it can be confirmed that when the target analyte 130 is oligomer type 1, a Raman analysis signal peak in the β-sheet structure is higher than a Raman analysis signal peak when the target analyte 130 is a monomer.

FIG. 11a is a TEM image illustrating oligomer type 2 of a target analyte according to an embodiment of the present invention, and FIG. 11b illustrates a Raman spectrum of oligomer type 2 of the target analyte according to an embodiment of the present invention.

Referring to FIGS. 11a and 11b, it can be confirmed that when a target analyte 130 bonded to a carboxylic acid-functionalized 3-dimensional SERS substrate 100 is more agglomerated than oligomer type 1 and thus becomes oligomer type 2, a Raman analysis signal peak in the β-sheet structure is remarkably higher than a Raman analysis signal peak in the α-helix structure.

In addition, it can be confirmed that when the target analyte 130 is oligomer type 2, a Raman analysis signal peak in the β-sheet structure is higher than a Raman analysis signal peak when the target analyte 130 is a monomer or oligomer type 1.

FIG. 12 is a TEM image illustrating a protofibril shape of a target analyte according to an embodiment of the present invention.

Referring to FIG. 12, it can be confirmed that the target analyte is further agglomerated beyond the state of oligomer type 2 to form a protofibril.

FIG. 13 is a TEM image illustrating a fibril shape of a target analyte according to an embodiment of the present invention.

Referring to FIG. 13, the target analyte 130 is further agglomerated beyond a protofibril state to form a fibril shape.

Accordingly, fibrillation information on the target analyte 130 may be obtained according to a Raman analysis signal generated through SERS using the carboxylic acid-functionalized 3-dimensional SERS substrate 100 according to an embodiment of the present invention.

Specifically, it may be confirmed from a Raman analysis signal generated through SERS using the carboxylic acid-functionalized 3-dimensional SERS substrate 100 according to an embodiment of the present invention how much the oligomer, protofibril or fibril of the target analyte 130 has progressed.

For a theoretical understanding of the Raman measurement results, it is desirable to view SERS analysis from the point of view of electromagnetic enhancement (EM) which is known to be a more important factor than chemical enhancement.

Incident electromagnetic radiation induces vibration dipoles in nanowires, and the dipoles intensify an incident laser by creating a strong local electric field on a surface.

At the same time, a scattered beam caused by vibrational transition of the target analyte 130 is enhanced by the same mechanism as an incident beam.

SERS enhancement considering the two contributions may be expressed by Equation 1 below:

$$\text{Electromagnetically enhanced } SERS \cong M_{Loc(w_L)} M_{Loc(w_R)} \quad \text{[Equation 1]}$$

In Equation 1, $M_{Loc(wL)}$ and $M_{Loc(wR)}$ are enhancement factors (EF) of local electric field strength at an excitation laser frequency and Raman frequency.

However, the target analyte 130 is not directly located in an enhanced local electromagnetic field region such as a laser-irradiated point.

Instead, the target analyte 130 is at most 50 nm away from the carboxylic acid-functionalized 3-dimensional SERS substrate 100.

It was found by prior studies that SERS intensity has a distance dependence of $1/r^{10}$ (r is a distance from a surface of the substrate 110 to the target analyte 130).

Nevertheless, the carboxylic acid-functionalized 3-dimensional SERS substrate 100 enables excellent SERS improvement because the metal nanowire array 121 constituting the three-dimensional nanostructure 120 is spread over a wide area.

Accordingly, most of the incident laser and scattered beam induce vibration dipoles and can contribute to enhancing the Raman analysis signal.

This can be proved by calculating reinforcement factors.

Among calculation methods of various enhancement factors such as a single-molecule enhancement factor (SMEF), a SERS substrate enhancement factor (SSEF), and an analytical enhancement factor (AEF), AEF is the most appropriate index for the carboxylic acid-functionalized 3-dimensional SERS substrate 100.

AEF may be expressed by Equation 2 below:

$$AEF = I_{SERS}/I \times C/C_{SERS} \quad \text{[Equation 2]}$$

In Equation 2, $I_{SERS}$ and $C_{SERS}$ represent the strength and concentration of the molecules of the target analyte 130 on the carboxylic acid-functionalized 3-dimensional SERS substrate 100, and $I_{RM}$ and $C_{RM}$ represent the strength and number of the molecules of the target analyte 130 on the substrate 110.

When $I_{SERS}=921$, $C_{SERS}=10^{-9}M$, $I_{RM}=166$, and $C_{RM}=10^{-4}M$, AEF is estimated to be $5.5 \times 10^5$.

This AEF value is the highest AEF value of the carboxylic acid-functionalized 3-dimensional SERS substrate 100 when a material constituting the substrate 110 is gold.

In addition, according to a prior report by Mubeen et. al., it can be seen that Raman analysis signal intensity is increased when a bottom surface of the substrate 110 is a thin gold film compared to when it is made of silicon.

In addition, according to prior reports, it can be confirmed that a gold substrate 110 can effectively reflect an excitation beam and a scattered beam, thereby contributing to the enhancement of a Raman signal.

Accordingly, it is desirable to use a gold substrate 110 as the substrate 110 of the carboxylic acid-functionalized 3-dimensional SERS substrate 100 according to an embodiment of the present invention.

Hereinafter, the present invention is described in more detail with reference to examples of demonstrating the characteristics and effects of the carboxylic acid-functionalized 3-dimensional SERS substrate according to an embodiment of the present invention. The following examples are only presented to experimentally prove the effects of the present invention, and the present invention is not limited by the following examples.

EXAMPLE

Master Mold Fabrication

A concave and convex pattern of a master mold was formed by direct self-assembly (DSA) of a block co-polymer.

A silicon wafer was patterned using KrF photolithography to prepare a guiding pattern having a depth of 40 nm, a width of 1 µm and a period of 1.25 µm.

Poly(styrene-b-dimethylsiloxane (PS-b-PDMS, molecular weight=48 kgmol$^{-1}$, fps=66.3%, polydispersity index (PDI)=1.19) purchased from Polymer Source Inc. was used as a block co-polymer.

After contacting PDMS-OH brush (5 kgmol$^{-1}$, Polymer Source Inc.) with the patterned silicon wafer, annealing was performed at 150° C. for 90 minutes in a vacuum chamber, and then an unreacted block co-polymer was removed by washing with toluene.

Next, PS-b-PDMS dissolved in toluene (0.8 wt %) was coated on the patterned silicon wafer.

BCP was solvent-annealed at room temperature for 12 hours using toluene vapor, and reactive ion etching (RIE) using CF$_4$ plasma (source power of 50 W, etching for 21 seconds) and O$_2$ plasma (source power of 60 W, etching for 30 seconds) was performed.

Operation pressure and gas flow rate were maintained at 15 mTorr and 30 sccm, respectively.

A master mold pattern has a trench width of 1 µm, a mesa sidewall width of 0.25 µm, and BCP stripes of a trench.

A master mold was manufactured to include 28 BCP stripes with a diameter of 15 nm and an interval of 20 nm.

Carboxylic Acid-Functionalized 3-Dimensional SERS Substrate Fabrication through Transfer Printing A 3-dimensional nanostructure was formed using a simple transfer printing process.

A PMMA solution composed of 4 wt % PMMA (MW 100,000) dissolved in a mixture of acetone and toluene was spin-coated on a master mold to be replicated.

The replicated PMMA was peeled off using a polyimide (PI) adhesive film.

Gold (Au) nanowires were formed by angle deposition of gold via electron beam evaporation on a PMMA replica.

Next, the gold nanowires were exposed to a vapor mixture of acetone and heptane for 20 seconds.

Because the adhesive force between the PMMA and the PI films was weakened due to the previous solvent annealing step, a single layer of gold nanowires was transfer printed to a PDMS pad, which is a polymer pad, to form a 3-dimensional nanostructure.

The substrate was a p-type Si wafer (Si substrate) or thin gold film-deposited p-type Si wafer (Au substrate).

Next, the 3-dimensional nanostructure was functionalized into carboxylic acid by an RIE process using an oxygen gas.

Accordingly, a carboxylic acid-functionalized 3-dimensional SERS substrate was fabricated.

Amine Coupling

Amine coupling was performed using EDC/NHS.

1-ethyl-3-(3-dimethylaminopropyl)-carbodiimide (EDC) and N-hydroxysuccinimide (NHS) as coupling agents were purchased from Sigma-Aldrich Inc.

EDC 20 mM and NHS 20 mM were dissolved in a (2-(N-morpholino)ethanesulfonic acid (MES) buffer solution and a phosphate-buffered saline (PBS) buffer solution. After concentrating both the buffer solutions to 1 M, the carboxylic acid-functionalized 3-dimensional SERS substrate was immersed in the buffer solution, cooled, and coupled with amine for 4 hours.

Materials and Characteristics

Both β-amyloid and tau protein were purchased from Sigma-Aldrich Inc.

An aptamer used to prove the superiority of the carboxylic acid-functionalized 3-dimensional SERS substrate was purchased from GenoTech Corp. (Daejeon, Korea).

Dispersive Raman spectroscopy (ARAMIS, Horiba) with excitation lasers at 514 nm and 785 nm was used for SERS measurement.

Raman analysis signals (SERS signals) measured by the dispersive Raman spectroscopy were collected for 5 seconds for the measurement of examples.

An enhanced local electromagnetic field of the carboxylic acid-functionalized 3-dimensional SERS substrate was measured by a scattering scanning near-field optical microscope (s-SNOM, Anasys, Instruments, CA, US) with a quantum cascade laser (QCL), excitation wavelengths were 1200 to 1800 $cm^{-1}$, and top-view images were obtained using a field emission scanning electron microscope (FE-SEM, Hitachi, S-4800).

Characteristic Evaluation

Confirmation of Amine Coupling and Target Analyte Immobilization

To confirm whether amine coupling was successfully performed and a target analyte was immobilized on a carboxylic acid-functionalized 3-dimensional SERS substrate, an oligonucleotide having an amine at the 5' end thereof and TAMRA at 3' end thereof was used.

TAMRA, a type of Raman dye, was used to eliminate the possibility of errors that may occur due to the small Raman cross-section area of a protein.

FIG. 14 illustrates RIE process time-dependent SERS spectra of a carboxylic acid-functionalized 3-dimensional SERS substrate according to an embodiment of the present invention.

Referring to FIG. 14, a surface of the carboxylic acid-functionalized 3-dimensional SERS substrate was etched with $O_2$ plasma to have various RIE times (0 sec, 30 sec, 60 sec, 90 sec).

At each RIE time condition, immobilization was carried out under conditions of 90 W source power, 45 W bias power and 15 mTorr gas pressure of 30 sccm flow.

After the RIE process, an amine coupling reaction through EDC/NHS was performed.

A TAMRA peak was not observed in a carboxylic acid-functionalized 3-dimensional SERS substrate which was not subjected to RIE (i.e., RIE time: 0 sec).

A characteristic peak of TAMRA appeared after a surface of the carboxylic acid-functionalized 3-dimensional SERS substrate was etched with $O_2$ plasma.

This demonstrates that the amine coupling reaction occurred between the oligonucleotide and the carboxylic acid-functionalized 3-dimensional SERS substrate surface.

The Raman analysis signal rapidly decreased with increasing RIE time, which is probably due to removal of the PMMA residue.

Detection Limit Concentration of Target Analyte

FIG. 15 illustrates target analyte concentration-dependent SERS spectra of a carboxylic acid-functionalized 3-dimensional SERS substrate according to an embodiment of the present invention.

Referring to FIG. 15, a Raman analysis signal of the carboxylic acid-functionalized 3-dimensional SERS substrate was measured while varying the concentration ($10^{-6}$M, $10^{-7}$M, $10^{-8}$M, $10^{-9}$M, $10^{-10}$M) of a target analyte.

As a result of Raman measurement, it was confirmed that a Raman analysis signal peak is higher with increasing concentration of the target analyte.

In addition, it can be confirmed that, when the concentration of the target analyte is $10^{-10}$M, a Raman analysis signal peak is hardly visible.

Accordingly, it can be confirmed that a detection limit concentration for a target analyte of the carboxylic acid-functionalized 3-dimensional SERS substrate is $10^{-10}$M.

SERS Analysis Dependent Upon Number of Laminated Metal Nanowire Arrays

FIG. 16 illustrates metal nanowire array lamination number-dependent SERS spectra of a carboxylic acid-functionalized 3-dimensional SERS substrate according to an embodiment of the present invention.

Here, "silicon wafer" spectra represent Raman spectrum results measured while increasing the number of metal nanowire arrays laminated on a silicon wafer.

In addition, "gold substrate" spectra represent Raman spectrum results measured while increasing the number of metal nanowire arrays laminated on a gold substrate.

Referring to FIG. 16, in both the silicon wafer and the gold substrate, the optimal lamination number of the metal nanowire arrays is 4.

However, when laminated more than 4 times, a different tendency is shown depending upon a substrate type.

FIG. 17 illustrates substrate type-dependent SERS intensity of a carboxylic acid-functionalized 3-dimensional SERS substrate according to an embodiment of the present invention.

Here, a SERS analysis signal intensity for each substrate type was measured at 1650 $cm^{-1}$.

In the case of the silicon wafer, the saturation of Raman analysis signal intensity started immediately after the fourth lamination, but in the case of the gold substrate, Raman analysis signal intensity decreased once significantly and then was saturated.

However, when the number of metal nanowire array layers exceeds four, a thin gold film on the bottom of the gold substrate effectively reflects a laser beam, thereby reducing the ability to improve the Raman analysis signal.

Accordingly, the metal nanowire array is laminated preferably 4 to 10 times, most preferably 4 times, on the substrate.

SERS Analysis of Carboxylic Acid-Functionalized 3-Dimensional SERS Substrate on which β-Amyloid or Tau Protein is Immobilized Label-free SERS measurement of β-amyloid and tau protein as biomarkers of Alzheimer's was performed using the unique properties of a carboxylic acid-functionalized 3-dimensional SERS substrate.

It is very difficult to obtain Raman spectra directly from proteins due to small Raman cross sections as well as complex chemical components.

However, several Raman spectrum characteristics were confirmed in both β-amyloid and tau protein by using the carboxylic acid-functionalized 3-dimensional SERS substrate.

Similar to the case of an aptamer, β-amyloid was immobilized on a surface of the carboxylic acid-functionalized 3-dimensional SERS substrate by an amine bond.

Since β-amyloid generally aggregates rapidly at room temperature, amine coupling was performed at 4° C. to avoid aggregation of β-amyloid.

A Raman spectrum of β-amyloid was measured in a spectral range of 800 $cm^{-1}$ to 1600 $cm^{-1}$.

FIG. 18 illustrates reaction time-dependent SERS spectra of a carboxylic acid-functionalized 3-dimensional SERS substrate according to an embodiment of the present invention.

Here, the reaction time means a time for which the carboxylic acid-functionalized 3-dimensional SERS substrate according to an embodiment of the present invention reacts with a target analyte.

Referring to FIG. 18, it can be confirmed that a reaction time between β-amyloid, as a target analyte, and the carboxylic acid-functionalized 3-dimensional SERS substrate according to an embodiment of the present invention does not change significantly after 4 hours.

In addition, it can be confirmed that various peaks appear in Raman spectra of β-amyloid.

It can be confirmed that in Raman spectra of FIG. 18, the Raman analysis signal peaks in 1270 $cm^{-1}$ band are most prominent.

A broad band of 1200 $cm^{-1}$ to 1340 $cm^{-1}$ designated as amide III includes information on a secondary structure of protein.

An amide III band mainly reflects $C_\alpha$—C stretching and C=O in-plane bending as well as N—H in-plane bending and C—N stretching.

Together with the amide I band and the amide II band, an amide III band provides information on a change in a protein structure.

However, the amide I band is poorly detected in SERS, and it is difficult to observe the amide II band under near-infrared (~785 nm) laser excitation due to the small Raman cross-section area of a protein.

The strong peak at 1270 $cm^{-1}$ shows that β-amyloid has an α-helix structure.

FIG. 19 illustrates β-amyloid concentration-dependent SERS spectra of a carboxylic acid-functionalized 3-dimensional SERS substrate according to an embodiment of the present invention.

Referring to FIG. 19, it can be confirmed that the α-helix structure of the β-amyloid structure is no longer dominant as the concentration of β-amyloid increases.

The α-helix structure, which is the original secondary structure of β-amyloid, tends to be misfolded, so that β-amyloid may be oligomerized.

Misfolded β-amyloid may often interact with other normal proteins to cause toxicity.

Since normal β-amyloid with α-helix structure mainly exists when the concentration of β-amyloid is low, a strong band may be confirmed at 1270 $cm^{-1}$ as a result of SERS analysis.

However, since the number of misfolded β-amyloids increases as the concentration of β-amyloid increases, it can be confirmed that rapid band increase is observed at 1145 $cm^{-1}$ and 1390 $cm^{-1}$ as the concentration of β-amyloid with a deformed α-helix structure increases.

FIG. 20 illustrates β-amyloid concentration-dependent SERS intensity according to an embodiment of the present invention.

Here, a graph denoted by ■ represents an intensity at 1270 $cm^{-1}$, a graph denoted by ● represents an intensity at 1390 $cm^{-1}$, and a graph denoted by ▲ represents an intensity at 1145 $cm^{-1}$.

Referring to FIG. 20, it can be confirmed that Raman analysis signal peaks become very strong in 1145 $cm^{-1}$ and 1390 $cm^{-1}$ bands as the concentration of β-amyloid increases.

A 1390 $cm^{-1}$ band called amide S band is due to Cα-H bending.

In the amide S band, it can be confirmed that the Raman analysis signal intensity is weak when a protein has a large Cα-H bending such as an α-helix.

However, it can be confirmed that Raman analysis signal intensity is strong in a β-sheet structure or a structure having small Cα-H bending such as a random coil.

In a band at 1145 $cm^{-1}$ due to Cα-C—N modification, it can be confirmed that a Raman analysis signal is intensified when the α-helix structure is deformed.

FIG. 21 illustrates tau protein concentration-dependent SERS spectra of a carboxylic acid-functionalized 3-dimensional SERS substrate according to an embodiment of the present invention.

In addition to β-amyloid, tau protein, which is another biomarker of Alzheimer's disease, on a surface of the carboxylic acid-functionalized 3-dimensional SERS substrate was observed by SERS.

Tau protein is abundant in the human brain and is involved in stabilizing microtubules.

Abnormal tau phosphorylation causes polypeptides to self-aggregate, resulting in fibrosis.

Tau protein consists of 441 amino acids and thus is the longest protein of six isomers.

Referring to FIG. 21, it can be confirmed that, despite the very complex chemical structure of the tau protein, the Raman spectrum thereof shows a peak at the same wavenumber with increasing concentration.

In addition, it can be confirmed that a band, such as an amide band, including structural information does not appear clearly in the Raman spectrum of the tau protein.

The secondary structure of tau protein is naturally unfolded or essentially disordered, which means that the content of secondary structures (α-helices and β-sheets) in the polypeptide chain thereof is low.

Accordingly, it can be confirmed that the amide III band is almost invisible when the concentration of tau protein is high, i.e., at a tau protein concentration of $10^{-7}$M.

It can be confirmed that both the appearance of the amide S band at 1390 $cm^{-1}$ and the appearance of the Cα-C—N modified band at 1145 $cm^{-1}$ are due to increase of tau protein with disordered structures.

Compared to β-amyloid, the Raman band of aromatic amino acid is well distinguished in the case of tau protein.

In particular, the phenylalanine (Phe) band of 1000 $cm^{-1}$ is not sensitive to structural changes, so it can be used for quantitative analysis of proteins without labeling.

Other Raman bands due to aromatic amino acids or peptide bonds were assigned based on the existing literature.

As described above, the carboxylic acid-functionalized 3-dimensional SERS substrate to be used for label-free SERS measurement of proteins enables protein structure analysis of SERS by simple spectroscopic analysis.

It can be confirmed that, compared with conventional analysis methods, such as NMR, small X-ray scattering (SAXS), and low-temperature EM, which require delicate sample preparation and complex analytical procedures, SERS measurement using the carboxylic acid-functionalized 3-dimensional SERS substrate according to the present invention has significant advantages.

Although the present invention has been described through limited examples and figures, the present invention is not intended to be limited to the examples. Those skilled in the art will appreciate that various modifications, additions, and substitutions are possible, without departing from the scope and spirit of the invention. Therefore, the scope of the present invention should not be limited by the embodiments, but should be determined by the following claims and equivalents to the following claims.

DESCRIPTION OF SYMBOLS

10: objective lens
100: carboxylic acid-functionalized 3-dimensional SERS substrate
110: substrate
120: 3-dimensional nanostructure
121: metal nanowire array
130: target analyte
131: oxygen gas
210: master mold
220: polymer mold
221: metal atom

The invention claimed is:

1. A carboxylic acid-functionalized 3-dimensional SERS substrate, comprising:
a substrate;
a 3-dimensional nanostructure comprising a multistacked metal nanowire array, wherein the multistacked metal nanowire array includes a plurality of single-layer metal nanowire arrays alternately stacked in a vertical direction on the substrate such that nanowires of a single-layer metal nanowire array among the plurality of single-layer metal nanowire arrays extend in a first horizontal direction perpendicular to the vertical direction, and nanowires of an adjacent single-layer metal nanowire array adjacent to the single-layer mental nanowire array among the plurality of single-layer metal nanowire arrays extend in a second horizontal direction perpendicular to each of the first horizontal direction and the vertical direction, and wherein the multistacked metal nanowire array is formed by repeatedly transfer printing a single-layer metal nanowire array, laminated on a polymer mold on which a pattern of a master mold is duplicated, onto the substrate; and
a functionalized carboxylic acid which is a carboxylic aid into which a residue of the polymer mold present on the 3-dimensional nanostructure is functionalized and which enables a target analyte to immobilize,
wherein the functionalized carboxylic acid includes a —COOH function group formed by substituting H for $CH_3$ in a —$COOCH_3$ functional group included in the residue of the polymer mold.

2. The carboxylic acid-functionalized 3-dimensional SERS substrate according to claim 1, wherein the functionalized carboxylic acid is the carboxylic acid into which a residue of a thin polymer film present on the 3-dimensional nanostructure is functionalized by a functionalization process.

3. The carboxylic acid-functionalized 3-dimensional SERS substrate according to claim 2, wherein the functionalized carboxylic acid includes the carboxylic acid having the —COOH function group formed by performing a reaction ion etching (RIE) process for the thin polymer film present on the 3-dimensional nanostructure.

4. The carboxylic acid-functionalized 3-dimensional SERS substrate according to claim 1, wherein the metal nanowire array of the 3-dimensional nanostructure is laminated 4 to 10 times.

5. The carboxylic acid-functionalized 3-dimensional SERS substrate according to claim 1, wherein metal nanowires in the metal nanowire array have a diameter of 25 nm to 50 nm.

6. A method of manufacturing a carboxylic acid-functionalized 3-dimensional SERS substrate, the method comprising:
forming a 3-dimensional nanostructure by (i) laminating a single-layer metal nanowire array on a polymer mold on which a pattern of a master mold is duplicated, (ii) transfer printing the single-layer metal nanowire array laminated on the polymer mold onto a substrate, and (iii) repeating the laminating and the transfer printing multiple times such that the multistacked metal nanowire array includes a plurality of single-layer metal nanowire arrays alternately stacked in a vertical direction on the substrate, nanowires of a single-layer metal nanowire array among the plurality of single-layer metal nanowire arrays extend in a first horizontal direction perpendicular to the vertical direction, and nanowires of an adjacent single-layer metal nanowire array adjacent to the single-layer mental nanowire array among the plurality of single-layer metal nanowire arrays extend in a second horizontal direction perpendicular to each of the first horizontal direction and the vertical direction;
forming a functionalized carboxylic acid by functionalizing a residue of the polymer mold present on the 3-dimensional nanostructure, wherein the functionalized carboxylic acid enables a target analyte to immobilize, and
modifying the functionalized carboxylic acid to an amine group through amine coupling reaction to immobilize the target analyte,
wherein the forming of the functionalized carboxylic acid includes substituting H for $CH_3$ in a —$COOCH_3$ functional group included in the residue of the polymer mold so that the functionalized carboxylic acid includes a —COOH function group.

7. The method according to claim 6, wherein the forming of the functionalized carboxylic acid comprises functionalizing a residue of a thin polymer film present on the 3-dimensional nanostructure into carboxylic acid by a functionalization process.

8. The method according to claim 6, wherein the amine coupling reaction is performed by reacting a coupling agent comprising 1-ethyl-3-(3-dimethylaminopropyl)-carbodiimide (EDC) and N-hydroxysuccinimide (NHS) with the functionalized carboxylic acid.

9. The method according to claim 6, wherein the amine coupling reaction is performed at 4° C. to 10° C. for 4 hours to 8 hours.

10. The method according to claim 6, wherein the target analyte comprises β-amyloid or tau protein.

11. The method according to claim 6, wherein a Raman analysis signal generated from the 3-dimensional nanostructure comprises fibrillation information on the target analyte.

12. The method according to claim 6, wherein the target analyte has a concentration of 10-12M or more.

13. The method according to claim 6, wherein the metal nanowire array of the 3-dimensional nanostructure is laminated 4 to 10 times.

14. The method according to claim 6, wherein metal nanowires in the metal nanowire array have a diameter of 25 nm to 50 nm.

15. The method according to claim 6, wherein the 3-dimensional nanostructure is formed by, after manufacturing the polymer mold using a thin polymer film and an adhesive film coated on a master mold on which a pattern is formed, forming the metal nanowire array on the polymer mold, and then selectively weakening adhesive force between the adhesive film and the polymer mold so that the metal nanowire array on the polymer mold is transfer printed onto the substrate.

16. The method according to claim 15, wherein the polymer mold is prepared by, after uniformly attaching the adhesive film to one surface of the thin polymer film formed on the master mold, separating the adhesive film-attached thin polymer film from the master mold.

17. The method according to claim 15, wherein the polymer mold and the adhesive film on which the metal nanowire array is formed are brought into contact with a polymer pad such that the metal nanowire array is in contact with the polymer pad, the polymer pad on which the metal nanowire array remains is brought into contact with the substrate such that the metal nanowire array is in contact with the substrate after separating the polymer mold and the adhesive film from the polymer pad such that the metal nanowire array remains on the polymer pad, and the polymer pad is separated from the substrate to be transfer printed.

18. A method of manufacturing a carboxylic acid-functionalized 3-dimensional SERS substrate, the method comprising:
forming a 3-dimensional nanostructure by (i) laminating a single-layer metal nanowire array on a polymer mold on which a pattern of a master mold is duplicated, (ii) transfer printing the single-layer metal nanowire array laminated on the polymer mold onto a substrate, and (iii) repeating the laminating and the transfer printing multiple times such that the multistacked metal nanowire array includes a plurality of single-layer metal nanowire arrays alternately stacked in a vertical direction on the substrate, nanowires of a single-layer metal nanowire array among the plurality of single-layer metal nanowire arrays extend in a first horizontal direction perpendicular to the vertical direction, and nanowires of an adjacent single-layer metal nanowire array adjacent to the single-layer mental nanowire array among the plurality of single-layer metal nanowire arrays extend in a second horizontal direction perpendicular to each of the first horizontal direction and the vertical direction;
forming a functionalized carboxylic acid by functionalizing a residue of the polymer mold present on the 3-dimensional nanostructure, wherein the functionalized carboxylic acid enables a target analyte to immobilize,
wherein the forming of the functionalized carboxylic acid includes substituting H for $CH_3$ in a —$COOCH_3$ functional group included in the residue of the polymer mold so that the functionalized carboxylic acid includes a —COOH function group.

19. The method according to claim 18, wherein the forming of the functionalized carboxylic acid comprises functionalizing a residue of a thin polymer film present on the 3-dimensional nanostructure by a functionalization process.

20. The method according to claim 18, wherein the forming of the carboxylic acid comprises performing a reaction ion etching (RIE) process for a thin polymer film present on the 3-dimensional nanostructure.

21. The method according to claim 18, wherein the laminating is performed 4 to 10 times.

22. The method according to claim 18, wherein metal nanowires in the metal nanowire array have a diameter of 25 nm to 50 nm.

23. The method according to claim 18, further comprising:
preparing the polymer mold using a thin polymer film and an adhesive film,
wherein the transfer printing comprises selectively weakening adhesive force between the adhesive film and the polymer mold so that the single-layer metal nanowire array on the polymer mold is transfer printed onto the substrate.

24. The method according to claim 23, wherein the preparing of the polymer mold comprises uniformly attaching the adhesive film to one surface of the thin polymer film formed on the master mold and separating the adhesive film-attached thin polymer film from the master mold.

25. The method according to claim 23, wherein (i) the polymer mold and the adhesive film on which the metal nanowire array is formed are brought into contact with a polymer pad such that the metal nanowire array is in contact with the polymer pad, (ii) the polymer mold and the adhesive film are separated from the polymer pad such that the metal nanowire array remains on the polymer pad, (iii) the polymer pad on which the metal nanowire array remains is brought into contact with the substrate such that the metal nanowire array is in contact with the substrate, and (iv) the metal nanowire array on the polymer pad is transfer printed onto the substrate by separating the polymer pad from the substrate.

* * * * *